United States Patent
Delgoffe

(10) Patent No.: US 12,048,717 B2
(45) Date of Patent: Jul. 30, 2024

(54) USE OF PEROXISOME PROLIFERATOR-ACTIVATED RECEPTOR GAMMA COACTIVATOR 1-ALPHA (PGC1α) AGONISTS TO IMPROVE EX VIVO EXPANSION OF TUMOR INFILTRATING LYMPHOCYTES (TILS)

(71) Applicant: University of Pittsburgh—Of the Commonwealth System of Higher Education, Pittsburgh, PA (US)

(72) Inventor: Greg M. Delgoffe, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 619 days.

(21) Appl. No.: 16/303,828

(22) PCT Filed: Jun. 5, 2017

(86) PCT No.: PCT/US2017/035928
§ 371 (c)(1),
(2) Date: Nov. 21, 2018

(87) PCT Pub. No.: WO2017/210677
PCT Pub. Date: Dec. 7, 2017

(65) Prior Publication Data
US 2019/0307796 A1    Oct. 10, 2019

Related U.S. Application Data
(60) Provisional application No. 62/345,076, filed on Jun. 3, 2016.

(51) Int. Cl.
| A61K 35/17 | (2015.01) |
| A61K 31/341 | (2006.01) |
| A61K 31/429 | (2006.01) |
| A61K 31/4439 | (2006.01) |
| A61K 31/498 | (2006.01) |
| A61K 31/5377 | (2006.01) |
| A61K 31/7056 | (2006.01) |
| A61K 38/17 | (2006.01) |
| A61K 38/20 | (2006.01) |
| A61K 39/00 | (2006.01) |
| A61K 39/39 | (2006.01) |
| A61K 45/06 | (2006.01) |
| A61P 35/00 | (2006.01) |
| C07K 16/28 | (2006.01) |
| C12N 5/0783 | (2010.01) |
| A61K 45/00 | (2006.01) |

(52) U.S. Cl.
CPC ............ *A61K 35/17* (2013.01); *A61K 31/341* (2013.01); *A61K 31/429* (2013.01); *A61K 31/4439* (2013.01); *A61K 31/498* (2013.01); *A61K 31/5377* (2013.01); *A61K 31/7056* (2013.01); *A61K 38/1774* (2013.01); *A61K 38/2013* (2013.01); *A61K 39/00119* (2018.08); *A61K 39/39* (2013.01); *A61K 45/06* (2013.01); *A61P 35/00* (2018.01); *C07K 16/2809* (2013.01); *C07K 16/2818* (2013.01); *C07K 16/2827* (2013.01); *C12N 5/0636* (2013.01); *A61K 2039/5158* (2013.01); *A61K 2039/876* (2018.08); *A61K 45/05* (2013.01); *A61K 2800/78* (2013.01); *C12N 2501/39* (2013.01); *C12N 2501/999* (2013.01)

(58) Field of Classification Search
CPC ............................ A61K 2800/78; A61K 35/17
See application file for complete search history.

(56) References Cited

U.S. PATENT DOCUMENTS

| 5,126,132 A | 6/1992 | Rosenberg |
| 2016/0023991 A1* | 1/2016 | Evans .................. C07D 209/34 514/236.5 |
| 2016/0039948 A1 | 2/2016 | Kufter et al. |
| 2016/0051653 A1 | 2/2016 | Strober et al. |

(Continued)

FOREIGN PATENT DOCUMENTS

| WO | WO 2012/031115 A2 | 3/2012 |
| WO | WO-2017223557 A1 * | 12/2017 ............. A61K 35/17 |

OTHER PUBLICATIONS

Yu et al. (Hepatology. Jan. 2006; 43 (1): 134-43).*

(Continued)

*Primary Examiner* — Stephen L Rawlings
(74) *Attorney, Agent, or Firm* — Klarquist Sparkman, LLP

(57) ABSTRACT

The present disclosure provides methods for expanding tumor-infiltrating lymphocytes (TILs), such as tumor-infiltrating T cells, utilizing an agonist of PGC1α in vivo, ex vivo, or both. Exhausted T cells present in the TIL population fail to effectively proliferate, produce cytokines, or kill target cells. The present disclosure provides methods to correct these defects through the use of pharmacologic agents to reprogram the metabolism of the exhausted intratumoral T cells. Exemplary agonists of PGC1α include proliferator-activated receptor (PPAR)-gamma agonists (e.g., a thiazolidinedione (TZD), aleglitazar, farglitazar, muraglitazar, or tesaglitazar), AMPK activators (e.g., 5-aminoimidazole-4-carboxamide ribonucleotide, AICAR), and sirtuin activators (e.g., resveratrol, SRT1720, SRT2104, SRT2183, SRT1460). Also provided are kits can compositions that can be used with such methods.

4 Claims, 7 Drawing Sheets

(56) References Cited

U.S. PATENT DOCUMENTS

2018/0228775 A1* 8/2018 Goyal ............... A61K 39/395

OTHER PUBLICATIONS

Miller et al. (Curr. Opin. Endocr. Metab. Res. Mar. 2019; 5: 37-44; author manuscript; pp. 1-13).*
Luconi et al. (Endocr Relat Cancer. Feb. 18, 2010; 17 (1): 169-77).*
Panigrahy et al. (Expert Opin. Investig. Drugs. Dec. 2003; 12 (12): 1925-37).*
Lee et al. (Curr. Oncol. Rep. Oct. 2012; 14 (5): 468-74).*
Bunt et al. (Cancer Immun. Immunother. 2013; 62: 225-36).*
Li et al. (J. Transl. Med. Oct. 26, 2010; 8: 104; pp. 1-15).*
Cellai et al. (Br. J. Cancer. Oct. 9, 2006; 95 (7): 879-88).*
Park et al. (J. Immunol. 2009; 183 (5): 3259-67).*
Hontecillas et al. (J. Immunol. 2007; 178: 2940-9).*
Bassaganya-Riera et al. (Gastroenterology. Sep. 2004; 127 (3): 777-91).*
Diab et al. (J. Immunol. 2002; 168: 2508-15).*
Hsiao et al. (Drug Saf. Aug. 2013; 36 (8): 643-9).*
Faas et al. (Biochim. Biophys. Acta Mol. Basis Dis. Oct. 1, 2020; 1866 (10): 165845; pp. 1-13).*
Miglio et al. (Neurochem. Int. Dec. 2009; 55 (7): 496-504).*
Pardo et al. (PLoS One. 2011; 6 (11): e26989; pp. 1-13).*
Corona et al. (Free Radic. Biol. Med. Nov. 2016; 100: 153-63).*
Bruin et al. (Endocrine. Apr. 2010; 37 (2): 303-11).*
Rong et al. (Diabetes. Jul. 2007; 56 (7): 1751-60).*
Deselm et al. (J. Surg. Oncol. Jul. 2017; 116 (1): 63-74).*
Saiki et al. (Int. J. Oncol. Aug. 2006; 29 (2): 437-43).*
Wang et al. (J. Biol. Chem. Aug. 30, 2002; 277 (35): 31781-8).*
Adurthi et al. (Int. J. Gynecol. Cancer. Sep. 2012; 22 (7): 1130-7).*
Deeg et al. (PPAR Res. 2008; 2008: 520465; pp. 1-6).*
Yan et al. (Immunol. Lett. Jan.-Feb. 2014; 157 (1-2): 9-15).*
Yu et al. (Asian Pacific J. Tropical Med. 2017; 10 (1): 64-8).*
Schmidt et al. (J. Leukoc. Biol. Mar. 2004; 75 (3): 478-85).*
Zhao et al. (Clin. Immunol. Oct. 2013; 149 (1): 119-32).*
Ferreira da Rocha Junior et al. (PPAR Res. 2013; 2013: 519724; pp. 1-9).*
Nisbet et al. (Am. J. Respir. Cell. Mol. Biol. Apr. 2010; 42 (4): 482-90).*
Bauer et al. (Am. J. Physiol. Lung Cell. Mol. Physiol. Sep. 2007; 293 (3): L580-2).*
Dennis (Nature. Aug. 7, 2006; 442: 739-741).*
Achert-Bicknell et al. (Endocrinology. Mar. 2009; 150 (3): 1330-40).*
Wilson-Fritch et al. (Mol. Cell. Biol. Feb. 2003; 23 (3): 1085-94).*
Zou et al. (PLoS One. 2013; 8 (9): e75139; pp. 1-12).*
Maldonado et al. (Adv. Immunol. 2010; 108: 111-65; author manuscript; pp. 1-45).*
Sakuishi et al. (Oncoimmunology. Apr. 1, 2013; 2 (4): e23849; pp. 1-9).*
Zhou et al. (Blood. Apr. 28, 2011; 117 (17): 4501-10; pp. 1-21).*
Komen et al. (Br. J. Pharmacol. Apr. 2014; 171 (8): 1818-36).*
Borra et al. (J. Biol. Chem. Apr. 29, 2005; 280 (17): 17187-95).*
Rong et al. (PPAR Res. 2011; 2011: 179454; pp. 1-12).*
Toseland et al. (Diabetes Obes. Metab. Jun. 2001; 3 (3): 163-70).*
Wei et al. (Cell Biol. Int. May 2018; 42 (5): 515-524).*
Lützen et al. (Naunyn Schmiedebergs Arch. Pharmacol. Jan. 2017; 390 (1): 37-48).*
Hou et al. (Eur. J. Pharmacol. Sep. 5, 2013; 715 (1-3): 196-203).*
Baldan et al.., "Efficient and reproducible generation of tumour-infiltrating lymphocytes for renal cell carcinoma," *Br J. Cancer* 112:1510-1518, 2015.
Bengsch et al., "Bioenergetic Insufficiencies Due to Metabolic Alterations Regulated by the Inhibitory Receptor PD-1 Are an Early Driver of CD8(+) T Cell Exhaustion," *Immunity 45*:358-373, 2016.
Chacon et al., "Manipulating the tumor microenvironment ex vivo for enhanced expansionof tumor-infiltrating lymphocytes for adoptive cell therapy," *Clin Cancer Res. 21*:611-621, 2015.
Rosenberg and Restifo, "Adoptive cell transfer as personalized immunotherapy for human cancer," *Science 348*:62-68, 2015.
Scharping and Delgoffe, "Tumor Microenvironment Metabolism: A New Checkpoint for Anti-Tumor Immunity," *Vaccines 4*:46, pp. 1-15, 2016.
Scharping et al., "The Tumor Microenvironment Represses T Cell Mitochondrial Biogenesis to Drive Intratumoral T Cell Metabolic Insufficiency and Dysfunction," *Immunity 45*:374-388, 2016.
International Search Report and Written Opinion mailed on Aug. 17, 2017 for International Application No. PCT/US2017/035928 (12 pages).
Bogacka et al., "Pioglitazone Induces Mitochondrial Biogenesis in Human Subcutaneous Adipose Tissue In Vivo" *Diabetes*, 54:1392-1399, 2005.
Knochelmann et al., "Modeling ex vivo tumor-infiltrating lymphocyte expansion from established solid malignancies" *Oncoimmunology*, 10(1): e1959101 (10 pages), 2021.
Rong et al., "Rosiglitazone Induces Mitochondrial Biogenesis in Differentiated Murine 3T3-L1 and C3H/10T1/2 Adipocytes" *PPAR Research*, 2011: 179454 (11 pages), 2011.
Ungvari et al., "Mitochondrial Protection by Resveratrol" *Exerc Sport Sci Rev*. 39(3): 128-132, 2011(Author Manuscript Version, 8 pages).

* cited by examiner

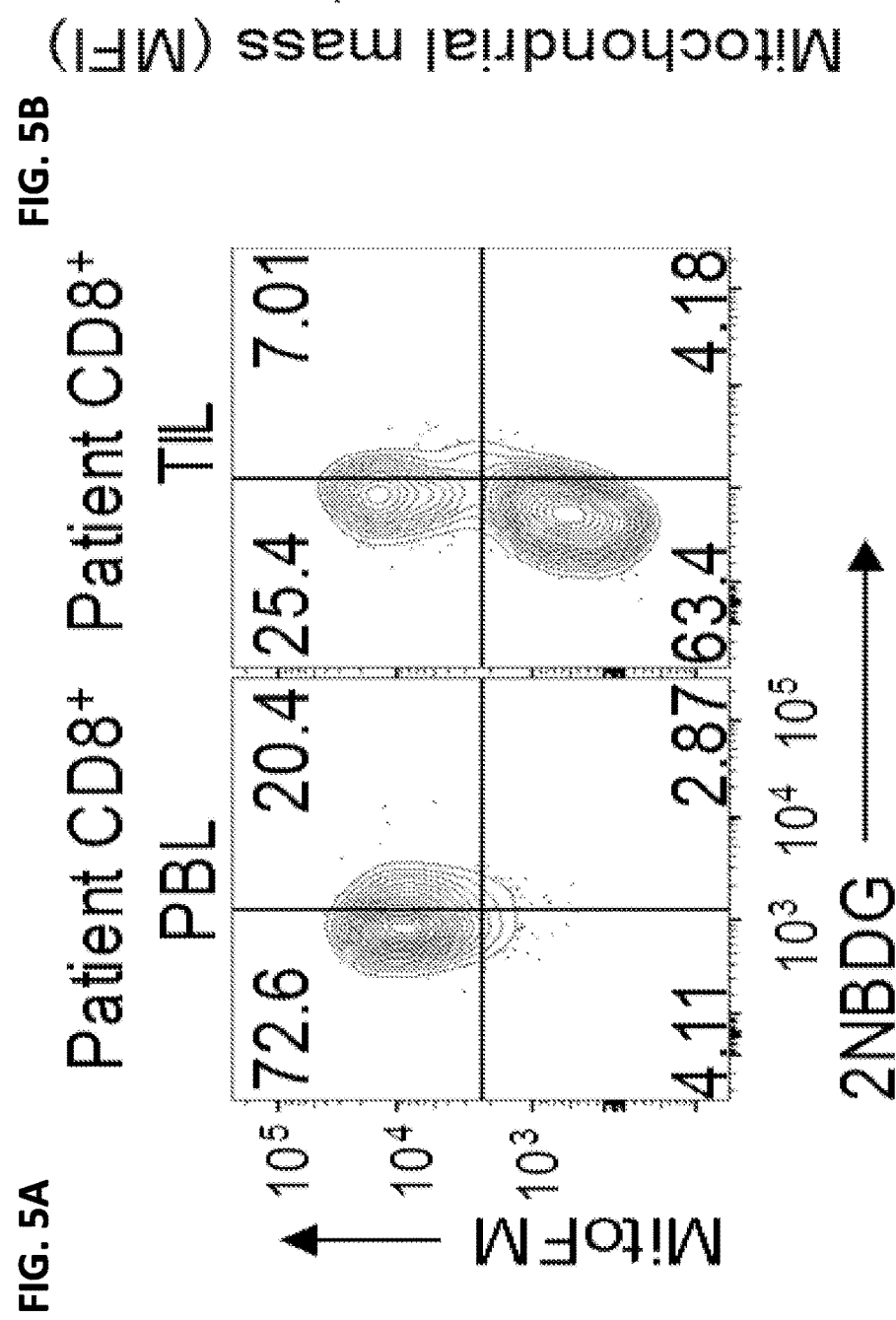

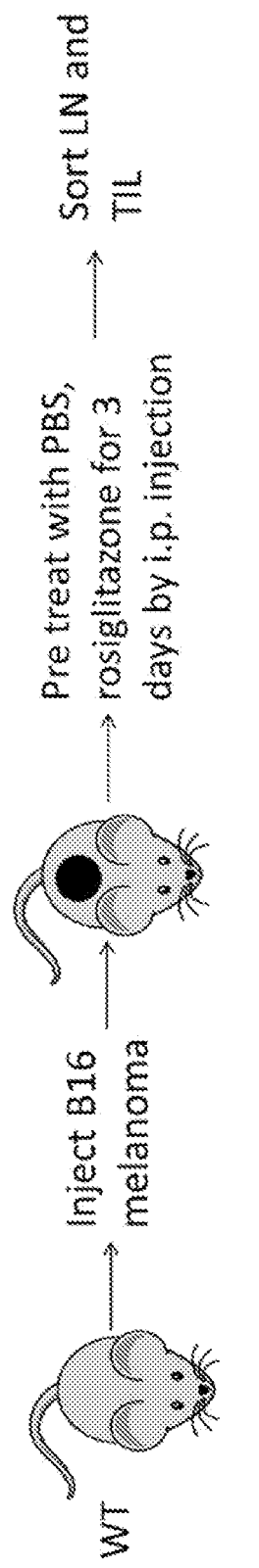
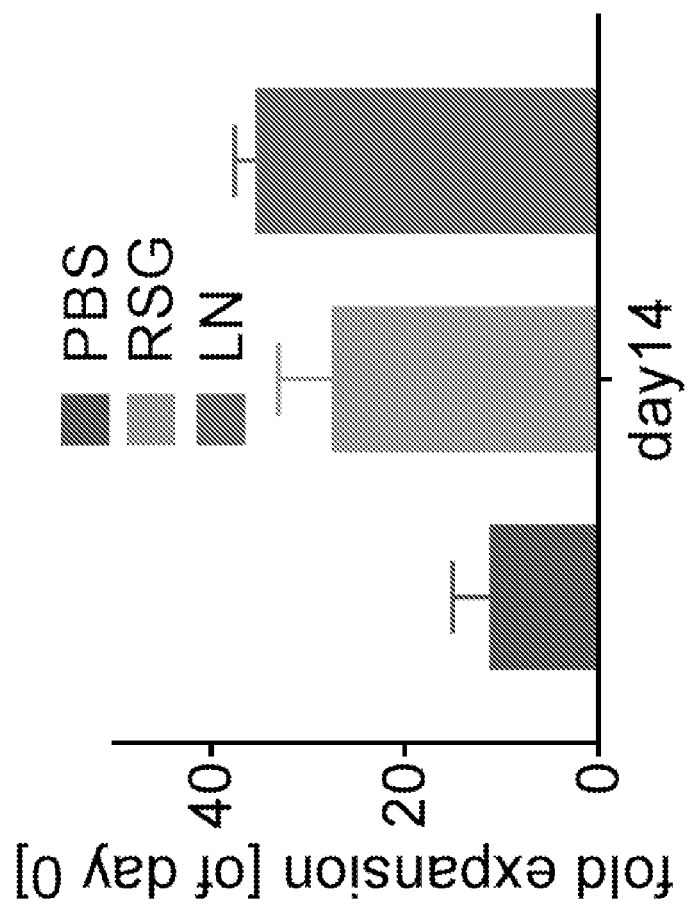

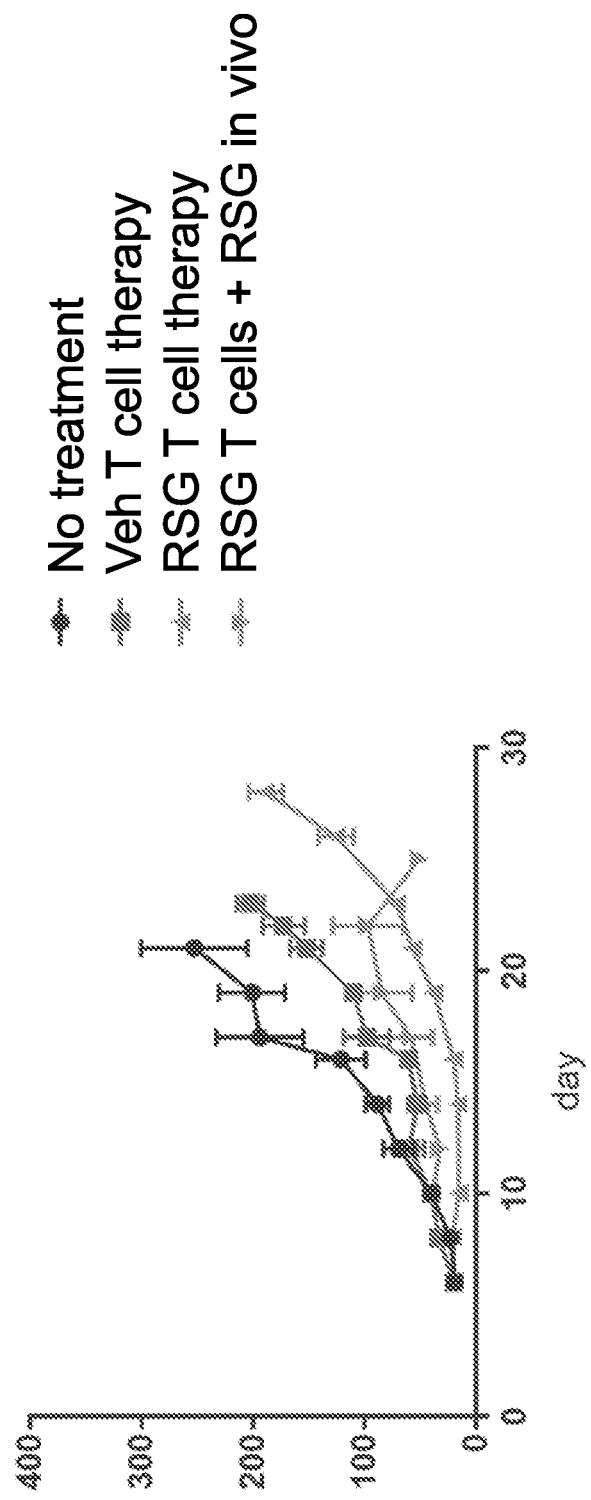

USE OF PEROXISOME PROLIFERATOR-ACTIVATED RECEPTOR GAMMA COACTIVATOR 1-ALPHA (PGC1α) AGONISTS TO IMPROVE EX VIVO EXPANSION OF TUMOR INFILTRATING LYMPHOCYTES (TILS)

CROSS-REFERENCE TO RELATED APPLICATION

This application claims priority to U.S. Provisional Application No. 62/345,076 filed Jun. 3, 2016, herein incorporated by reference.

FIELD

The present disclosure provides methods for expanding tumor-infiltrating lymphocytes (TILs), such as tumor-infiltrating T cells, utilizing an agonist of PGC1α. Also provided are kits can compositions that can be used with such methods.

BACKGROUND

Cancer cells evade immune destruction in part by generating an immunosuppressive microenvironment, composed of suppressive cytokines, co-inhibitory molecule ligands, altered stromal cell populations, and the recruitment of regulatory populations such as myeloid-derived suppressor cells and regulatory T cells[1]. It has also become clear that the metabolic makeup of the tumor microenvironment serves as a critical barrier to antitumor immunity[2, 3, 4]. As T cell activation is a bioenergetically demanding process, a lack of available nutrients can represent a key mechanism by which tumors control immunity and continue progress unimpeded[2, 3, 4].

Adoptive T cell therapies have emerged as a viable immunotherapeutic tool for cancer therapy (e.g., see Rosenberg and Restifo, Science, 348:62-8, 2015). One form of adoptive cell therapy for cancers is tumor infiltrating lymphocyte (TIL) therapy. TIL therapy relies on ex vivo expansion of T-cells isolated from a resected tumor. After multiple rounds of in vitro expansion, the cells are re-infused into the patient to promote regression at tumors and metastases. Unfortunately, adoptive TIL therapy only provides benefit for a subset of patients that receive it, and many times fails due to poor T cell expansion in vitro.

SUMMARY

It is shown herein that tumor-infiltrating T cells display crippling metabolic defects characterized most prominently by a loss of mitochondrial function and mass. This loss is progressive and correlates with T cell exhaustion, but occurs largely independently of PD-1 signaling. Rather, tumor microenvironment-derived signals drive down the expression of PGC1α, a key transcriptional co-activator in the generation of new mitochondria. Restoration of PGC1α expression in T cells prevents the exhaustion phenotype induced by the tumor-microenvironment. Thus, the metabolic capacity of tumor-infiltrating T cells appears to be highly suppressed by the tumor microenvironment, and these effects are stable even when they are removed from that environment. Thus, immunotherapeutic approaches which utilized T cells that have previously been in this harsh microenvironment have substantial metabolic hurdles to overcome to achieve success.

Provided herein are methods that can be used to improve cellular immunotherapy, specifically adoptive tumor-infiltrating lymphocyte (TIL) therapy. For example, the disclosure provides new methods for treating or restoring exhausted tumor infiltrating lymphocytes (TILs), such as tumor infiltrating T-cells, ex vivo, in vivo, or both, which utilize effective amounts of one or more agents that increase peroxisome proliferator-activated receptor gamma coactivator 1-alpha (PGC1α) activity in the TILs. In some examples, the TILs from the tumor include exhausted tumor infiltrating T-cells, such as those having sustained expression of PD-1, sustained expression of LAG-3, sustained expression of Tim-3, reduced mitochondrial mass, reduced expression of PGC1α, or combinations thereof.

In some examples, the methods are at least partially performed ex vivo. For example, such methods can include incubating TILs (such as those obtained or harvested from a tumor in a subject) in the presence of the PGC1a agonist in culture, under conditions that allow for ex vivo expansion of the TILs and restoration of the exhausted tumor-infiltrating T-cells, such as a period of days or weeks (such as at least 1 week, at least 2 weeks, at least 3 weeks, at least 4 weeks, or at least 6 weeks). In some examples, the method includes monitoring the TILs, for example determining the number of TILs, determining or measuring the mitochondrial activity and/or mass of the TILs, and/or determining or measuring expression of one or more of PGC1α, PD-1, LAG-3, and Tim-3 in the TILs. In some examples, the TILs are allowed to expand until billions of TILs are obtained, such as tens of billions TILs.

In some examples, the methods are at least partially performed in vivo. For example, such methods can include administering an effective amount of the one or more agents that increase PGC1a activity in the TILs to a subject with the tumor. Such administration can occur over a period of days or weeks (such as at least 1 day, at least 2 days, at least 3 days, at least 4 days, at least 5 days, at least 6 days, at least 1 week, at least 2 weeks, at least 3 weeks, at least 4 weeks, or at least 6 weeks). In some examples, the method further includes harvesting, obtaining, and/or isolating TILs from the tumor and then expanding the harvested TILs ex vivo (wherein the expanding can occur in the presence or absence of one or more agents that increase PGC1a activity), such as a period of days or weeks (such as at least 1 week, at least 2 weeks, at least 3 weeks, at least 4 weeks, or at least 6 weeks).

Expansion of the TILs ex vivo can further include contacting the TILs from the tumor with interleukin 2 (IL-2), anti-CD3, anti-CD28, or combinations thereof. In some examples, the anti-CD3 and the anti-CD28 are present on (e.g., attached to) a bead.

In some examples, TILs from the tumor are isolated prior to expanding them ex vivo (for example in the presence of the PGC1α agonist(s)), for example by isolating CD8+ T cells from the tumor (e.g., using flow cytometry). The resulting CD8+ T cells from the tumor can then be expanded ex vivo, for example in the presence of the PGC1α agonist(s) (and optional other agents such as IL-2, anti-CD3, and/or anti-CD28). In some examples, a portion of the tumor from the subject is incubated with the PGC1α agonist(s) (and optional other agents such as IL-2, anti-CD3, and/or anti-CD28), under conditions that allow reproduction of the T cells (and rescue of the exhausted tumor infiltrating T-cells) in the tumor sample. In some examples, the subject is first administered an effective amount of one or more PGC1α agonist(s), and subsequently a portion of the tumor from the subject (such as isolated TILs from the tumor) is incubated with the PGC1α agonist(s) (and optional other agents such as IL-2, anti-CD3, and/or anti-CD28), under conditions that allow reproduction of the T cells (and rescue of the exhausted tumor infiltrating T-cells) in the tumor sample. In some examples, the subject is first administered an effective amount of one or more PGC1α agonist(s), and subsequently a portion of the tumor from the subject (such as isolated TILs from the tumor) is incubated under conditions that allow reproduction of the T cells (and rescue of the exhausted tumor infiltrating T-cells) in the tumor sample, for example in the presence of IL-2, anti-CD3, and/or anti-CD28).

Also provided are isolated TILs expanded or treated using the disclosed methods. In some examples, such expanded TILs are restored tumor-infiltrating T-cells that were previously exhausted (e.g., have increased expression of PGC1α relative to their exhausted state). In some examples, the isolated TILs expanded using the disclosed methods are present in a pharmaceutically acceptable carrier, such as saline solution, or in a growth media, or in a preservative, such as DMSO. In some examples, the isolated TILs expanded using the disclosed methods are cryopreserved.

Expanded TILs generated using the disclosed methods can be used in cancer immunotherapy, for example to treat a tumor in vivo. For example, effective amount of the expanded TILs generated using the methods herein are administered to the subject, thereby treating a tumor (such as a primary tumor and/or a metastasis) in the subject. In some examples, such subjects are also administered an effective amount of IL-2 to the subject before, after, or both before and after, administering the expanded TILs. In some examples, such subjects are administered an effective amount of one or more PGC1α agonists to the subject before, after, or both before and after, administering the expanded TILs. In some examples, the subject is administered an effective amount of nonmyeloablative chemotherapy or radiotherapy to deplete native lymphocytes prior to administering an effective amount of the expanded TILs. In some examples, the subject is one who has not previously responded to a PD-1 antagonist or PD-L1 antagonist therapy. Such methods can treat the tumor in the subject by reducing the volume or weight of the tumor, reducing the number of metastases, reducing the size or weight of a metastasis, or combinations thereof. Exemplary tumors that can be treated with the disclosed methods and kits include, but are not limited to, colorectal cancer, melanoma, cervical cancer, lung cancer, ovarian cancer, bladder cancer, breast cancer, or head and neck cancer.

Also provided are compositions and kits that can be used with the disclosed methods. In some examples, the composition or kits includes one or more agents that increase PGC1α activity and one or more of anti-CD3, anti-CD28, and IL-2. In some examples, in a kit, such reagents are present in a separate container. In one example, the anti-CD3 and anti-CD28 are in the same container, and may be present on a bead for example.

Examples of agents that increase PGC1α activity (e.g., PGC1α agonists), which can be used in the disclosed methods and kits, include but are not limited to, peroxisome proliferator-activated receptor (PPAR)-gamma agonists, AMPK activators, sirtuin activators, as well as combinations thereof. Exemplary PPAR-γ agonists include thiazolidinediones (TZDs), aleglitazar, farglitazar, muraglitazar, and tesaglitazar. Exemplary TZDs include pioglitazone, rosiglitazone, rivoglitazone, and troglitazone. Exemplary AMPK activators include 5-aminoimidazole-4-carboxamide ribonucleotide (AICAR). Exemplary sirtuin activators include resveratrol, SRT1720, SRT2104, SRT2183, SRT1460, and combinations thereof.

The foregoing and other objects and features of the disclosure will become more apparent from the following detailed description, which proceeds with reference to the accompanying figures.

BRIEF DESCRIPTION OF THE DRAWINGS

FIGS. 5A-5B. Human TIL lose mitochondrial mass. A, Mitochondrial mass (MitoTracker® FM fluorescent dye staining) and glucose uptake (2NBDG staining) of $CD8^+$ T cells infiltrating TIL isolated from head and neck squamous cell carcinoma patients. B, Data as in A tabulated from multiple patients. *, $p<0.05$ by unpaired t-test.

FIGS. 6A-6B: Expansion of Tumor infiltrating T cells is enhanced with rosiglitazone (RSG). A, Overview of the method. Mice were injected with B16 melanoma cells, and then subsequently injected with PBS or RSG for 3 days. Lymph nodes (LN) and TILs were then harvested and expanded ex vivo in the presence of IL2 for up to 14 days.

Figure 1A:
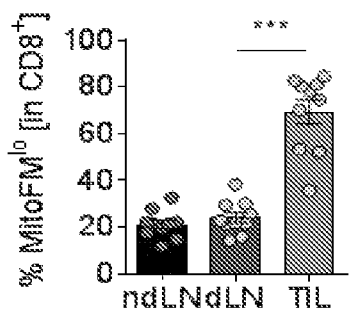
FIGS. 1A-1G. $CD8^+$ T cells from display a crippling loss of mitochondrial mass due to repression of PGC1α-mediated mitochondrial biogenesis. A, MitoTracker® FM fluorescent dye staining of mitochondrial mass in $CD8^+$ T cells isolated from C57BL/6 mice bearing d12 B16 melanoma tumors (ndLN: nondraining lymph node, dLN: draining LN, TIL: tumor infiltrating lymphocytes). B, Transmission electron micrograph of mitochondrial mass and morphology from effector or tumor-infiltrating T cells. C, Mitochondrial mass as a function of co-inhibitory molecule expression. D, ATP concentrations from T cells sorted from LN or TIL as indicated. E, Flow cytogram of PGC1α in $CD8^+$ T cells isolated as indicated. F, Mitochondrial mass and G, IFNγ production of OT-I×Thy1.1$^+$ T cells retrovirally transduced with a PGC1α-overexpressing construct or its empty control and transferred into mice expressing $B16^{OVA}$ tumors. *, $p<0.05$, $p<0.01$, *, $p<0.001$ by unpaired t-test.

B, Bar graph showing fold of ex vivo expansion of tumor infiltrating T cells from mice injected with PBS or RSG and ex vivo expansion of LNs at day 14.

FIG. 7: Use of RSG-Expanded Tumor infiltrating T cells in combination with RGS in vivo treatment enhance in vivo treatment of tumors. Graph shows size of tumor over days.

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jun. 3, 2016) are herein incorporated by reference.

In order to facilitate review of the various embodiments of the disclosure, the following explanations of specific terms are provided:

Administration: To provide or give a subject an agent, such as a PGC1□ agonist and TILs expanded using the disclosed methods, by any effective route. Exemplary routes of administration include, but are not limited to, injection (such as subcutaneous, intramuscular, intradermal, intraperitoneal, intratumoral, and intravenous), transdermal, intranasal, and inhalation routes.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Contact: Placement in direct physical association, including a solid or a liquid form. Contacting can occur in vitro or ex vivo, for example, by adding a reagent (such as one or more PGC1α agonists) to a sample (such as one containing TILs), or in vivo by administering a reagent (such as one or more PGC1α agonists or expanded TILs) to a subject.

Effective amount: The amount of an agent (such as a PGC1α agonist or TILs expanded using the disclosed methods) that is sufficient to effect beneficial or desired results.

A therapeutically effective amount may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" (e.g., of TILs expanded using the disclosed methods) is an amount sufficient to reduce the volume/size of a tumor, the weight of a tumor, the number of metastases, reduce the volume/size of a metastasis, the weight of a metastasis, or combinations thereof, for example by at least 10%, at least 20%, at least 25%, at least 50%, at least 70%, at least 75%, at least 80%, at least 90%, at least 95%, or at least 99% (as compared to no administration of the therapeutic agent). In one embodiment, an "effective amount" (e.g., of a PGC1α agonist) is an amount sufficient to increase the activity and/or expression of PGC1α in an exhausted tumor-infiltrating T cell, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the therapeutic agent).

Exhausted tumor-infiltrating T-cell: A TIL T cell that is activated chronically (as in cancer and in chronic viral infections), which succumb to a persistent phenotype of hyporesponsiveness. Such exhausted cells typically have chronic activation or sustained expression of PD-1, LAG-3, and Tim-3, and reduced expression of PGC1α (such as a reduction of at least 10%, at least 20%, at least 25%, at least 50%, at least 70%, at least 75%, or at least 80%, as compared to a non-exhausted tumor-infiltrating T-cell). In some examples, exhausted tumor-infiltrating T-cells have reduced mitochondrial mass (such as a reduction of at least 10%, at least 20%, at least 25%, at least 50%, at least 70%, at least 75%, at least 80%, or at least 90% as compared to a non-exhausted tumor-infiltrating T-cell), and/or reduced mitochondrial activity (such as a reduction of at least 10%, at least 20%, at least 25%, at least 50%, at least 70%, at least 75%, at least 80%, or at least 90% as compared to a non-exhausted tumor-infiltrating T-cell). Such activity can result in a difficulty of these cells to expand, for example ex vivo. The present disclosure provides methods to correct these defects (thereby resulting in a restored TIL or restored TIL T cell, e.g., has increased expression of PGC1α (such as an increase of at least 10%, at least 20%, at least 25%, at least 50%, at least 70%, at least 75%, at least 80%, at least 90%, at least 100%, or at least 300%, as compared to the exhausted tumor-infiltrating T-cell prior to treatment); increased mitochondrial mass (such as an increase of at least 10%, at least 20%, at least 25%, at least 50%, at least 70%, at least 75%, at least 80%, at least 90%, at least 100%, or at least 300%, as compared to the exhausted tumor-infiltrating T-cell prior to treatment); and/or increased mitochondrial activity (such as an increase of at least 10%, at least 20%, at least 25%, at least 50%, at least 70%, at least 75%, at least 80%, at least 90%, at least 100%, or at least 300%, as compared to the exhausted tumor-infiltrating T-cell prior to treatment) through the use of pharmacologic agents to reprogram the metabolism of the exhausted intratumoral T cells.

Increase or Decrease: A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated: An "isolated" biological component (such as TILs expanded using the disclosed methods) has been substantially separated, produced apart from, or purified away from other biological components in the cell or tissue of an organism in which the component occurs, such as other cells (e.g., tumor cells), chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated TILs expanded using the disclosed methods in some examples are at least 50% pure, such as at least 75%, at least 80%, at least 90%, at least 95%, at least 98%, or at least 100% pure.

Lymphocyte-activation gene 3 (LAG-3): (e.g., OMIM 153337) A cell surface molecule with diverse biologic effects on T cell function. LAG-3 is expressed on activated T cells, natural killer cells, B cells and plasmacytoid dendritic cells. LAG3's main ligand is MHC class II. The protein negatively regulates cellular proliferation, activation, and homeostasis of T cells, in a similar fashion to CTLA-4 and PD-1 and has been reported to play a role in Treg suppressive function. LAG-3 is an inhibitory receptor that mediates T-cell exhaustion. The human form is a 503 aa type 1 transmembrane protein with four extracellular Ig-like domains. LAG-3 sequences are publically available, for example from the GenBank® sequence database (e.g., Accession Nos. NP_002277.4 (mature peptide is aa 23-525), NP_032505.1 (mature peptide is aa 23-521), ABI58233.1, and AAP57397.1 provide exemplary LAG-3 protein sequences, while Accession Nos. NM_002286.5, DQ859925.1, NM_008479.2 and AY230414.1 provide exemplary LAG-3 nucleic acid sequences). One of ordinary skill in the art can identify additional LAG-3 nucleic acid and protein sequences, including LAG-3 variants, such as those having at least 80%, at least 85%, at least 90%, at least 92%, at least 95%, at least 98%, or at least 99% sequence identity to these GenBank® sequences.

Programmed cell death protein 1 (PD-1 or CD279) (e.g., OMIM 600244): A cell surface receptor that belongs to the immunoglobulin superfamily and is expressed on T cells and pro-B cells. PD-1 binds two ligands, PD-L1 and PD-L2. The human form is a 268 aa type 1 transmembrane protein. PD-1 is an inhibitory receptor that mediates T-cell exhaustion. PD-1 sequences are publically available, for example from the GenBank® sequence database (e.g., Accession Nos. NP_005009.2 (mature peptide is aa 21-288), CAA48113.1, NP_001301026.1 (mature peptide is aa 25-288), and CAA48113.1 (mature peptide is aa 21-288) provide exemplary PD-1 protein sequences, while Accession Nos. L27440.1, NM_005018.2, X67914.1, AB898677.1 and EU295528.2 provide exemplary PD-1 nucleic acid sequences). One of ordinary skill in the art can identify additional PD-1 nucleic acid and protein sequences, including PD-1 variants, such as those having at least 80%, at least 85%, at least 90%, at least 92%, at least 95%, at least 98%, or at least 99% sequence identity to these GenBank® sequences.

Peroxisome proliferator-activated receptor (PPAR) gamma coactivator 1-alpha (PGC1α): (e.g., OMIM 604517): A transcriptional coactivator that regulates the genes involved in energy metabolism. PGC-1a is a regulator of mitochondrial biogenesis and function. A PGC1α agonist includes agents that increase the expression and/or biological activity of PGC1α. PGC-1a sequences are publically available, for example from the GenBank® sequence database (e.g., Accession Nos. NP_037393.1, NP_032930.1, and NP_112637.1 provide exemplary PGC-1α protein sequences, while Accession Nos. NM_013261.3, NM_008904.2, and NM_031347.1 provide exemplary PGC-1a nucleic acid sequences). One of ordinary skill in the art can identify additional PGC-1α nucleic acid and protein sequences, including PGC-1α variants, such as those having at least 80%, at least 85%, at least 90%, at least 92%, at least 95%, at least 98%, or at least 99% sequence identity to these GenBank® sequences.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of an PGC1α agonist or TILs expanded using the disclosed methods. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a tumor, such as a cancer, that can be treated using the TILs expanded using the disclosed methods. In some examples, the subject is a laboratory animal/organism, such as a mouse, rabbit, or rat.

T-cell immunoglobulin and mucin-domain containing-3 (Tim-3). Also known as hepatitis A virus cellular receptor 2 (HAVCR2): (e.g., OMIM 606652): A Th1-specific cell surface protein that regulates macrophage activation. An inhibitory receptor that mediates T-cell exhaustion. Tim-3 sequences are publically available, for example from the GenBank® sequence database (e.g., Accession Nos. NP_116171.3 (mature protein aa 22-301), NP_599011.2 (mature protein aa 20-281), and 001094232.1 (mature protein aa 22-282) provide exemplary Tim-3 protein sequences, while Accession Nos. NM_032782.4, NM_134250.2, and NM_001100762.1 provide exemplary Tim-3 nucleic acid sequences). One of ordinary skill in the art can identify additional Tim-3 nucleic acid and protein sequences, including Tim-3 variants, such as those having at least 80%, at least 85%, at least 90%, at least 92%, at least 95%, at least 98%, or at least 99% sequence identity to these GenBank® sequences.

Therapeutic agent: Refers to one or more molecules or compounds that confer some beneficial effect upon administration to a subject. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed methods results in a decrease in the number, volume, and/or weight of a tumor and/or metastases.

Tumor-infiltrating lymphocytes (TILs): White blood cells that have left the bloodstream and migrated into a tumor. They are mononuclear immune cells, and can include a mixture of different types of cells (e.g., T cells, B cells, NK cells, macrophages) in variable proportions, with T cells usually being the most abundant. In some examples, a TIL expanded using the disclosed methods is a T cell, such as an exhausted tumor-infiltrating T-cell.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated with the TILs expanded using the disclosed methods include solid tumors, such as breast carcinomas (e.g. lobular and duct carcinomas, such as a triple negative breast cancer), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, head and neck squamous cell carcinoma, and lymphatic tumors (including B-cell and T-cell malignant lymphoma). In one example, the tumor is an adenocarcinoma.

The methods can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

Under conditions sufficient for: A phrase that is used to describe any environment that permits a desired activity. In one example the desired activity is increased expression or activity of PGC1α, for example in an exhausted tumor-infiltrating T-cell. In one example the desired activity is treatment of a tumor in vivo, for example using the expanded TILs generated using the disclosed methods.

Overview

Recent advances in the clinic have revealed that immunotherapy will likely shift the paradigm of how cancer is treated. While checkpoint blockade (anti-CTLA-4, anti-PD-1, and others in development) and chimeric antigen receptor T cell therapy have much success and attention in recent years,[7] some of the first successful cancer immunotherapies were adoptive cell therapies using T cells isolated from tumor-infiltrating lymphocytes (TIL). Adoptive TIL therapy operates under the notion that by virtue of T cells being in the tumor, they are likely specific for tumor antigens[8]. Thus, adoptive TIL therapy includes removal of T cells from a surgical resection, which are activated in vitro using tumor lysate (as well as polyclonally) in the presence of cytokines which can induce their proliferation. After several days/weeks in culture, the expanded T cells are then infused back into the patient to treat primary tumors and distant metastases. Adoptive TIL therapy has had a few notable successes but, like many immunotherapies, the majority of patients currently receive little benefit, despite the fact that they receive a massive infusion of in vitro expanded T cells[5,6,9]. This may be due in part to the fact that all T cells isolated from the tumor are expanded together in a relatively non-specific manner, and that less tumor-reactive T cells tend to outproliferate the others. T cells that are activated chronically (as in cancer and in chronic viral infections) succumb to a persistent phenotype of hyporesponsiveness termed T cell 'exhaustion.'[10] These exhausted T cells express progressively high levels of co-inhibitory 'checkpoint' molecules like PD-1, LAG-3, and Tim-3, and fail to effectively proliferate, produce cytokines, or kill target cells. However, the nature of their inherent dysfunction remains the subject of much study.

Thus, the most exhausted intratumoral T cells may be the most desirable T cell for adoptive therapy as they responded with such vigor initially. However, their 'metabolically exhausted' nature prevents effective expansion, resulting in a final cellular product that is dominated by less responsive T cells that have outproliferated their exhausted brethren (FIGS. 1A-1G). The present disclosure provides methods to correct these defects through the use of pharmacologic agents to reprogram the metabolism of the exhausted intratumoral T cells. The methods give the exhausted T cells a proliferative edge in vitro, such that they represent a larger proportion of the T cells for re-infusion, tipping the balance in favor of anti-tumor immunity and tumor regression.

Figure 1B:
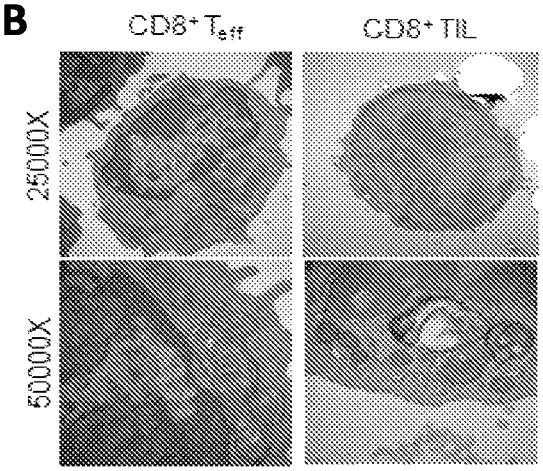
Figure 1C:
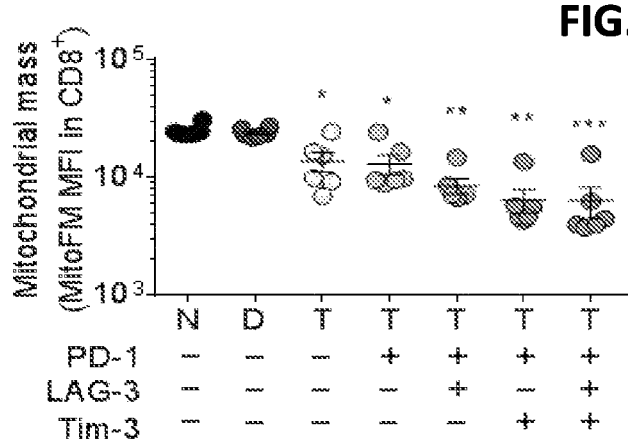
Figure 1D:
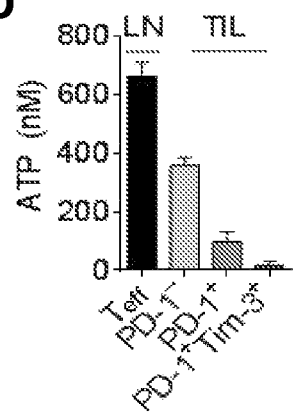
Figure 1E:
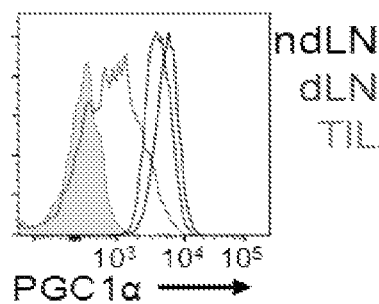
Figure 1F:
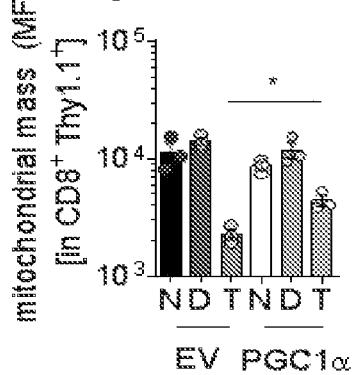
Figure 1G:
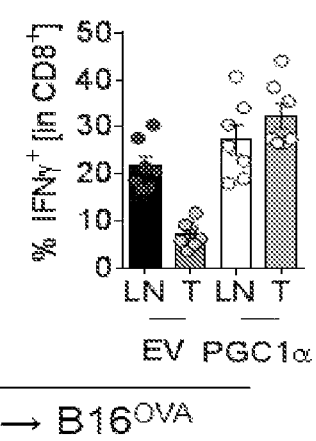

T cell activation is extremely metabolically demanding, and metabolism represents a key mechanism by which T cells can be regulate[11]. It has been determined that tumor-infiltrating T cells display fundamental metabolic defects, characterized most prominently by a crippling loss of mitochondrial function and mass (FIGS. 1A, 1B). This loss is progressive, correlating with upregulation of co-inhibitory molecules, but occurs independently of PD-1 signaling (FIGS. 1C, 1D). Rather, T cells infiltrating tumors fail to initiate programs to generate new mitochondria, displaying repressed expression of the transcriptional co-activator PGC1α, critical for the initiation of mitochondrial biogenesis[12, 13] (FIG. 1E). Restoration of PGC1α function rescues T cell function and mitochondrial activity in the tumor microenvironment (FIGS. 1F, 1G). Thus, T cell exhaustion has metabolic underpinnings: in addition to checkpoint signaling and immunosuppressive cytokines, there are basic cellular defects that prevent intratumoral exhausted T cells from fully functioning.

Figure 2A:
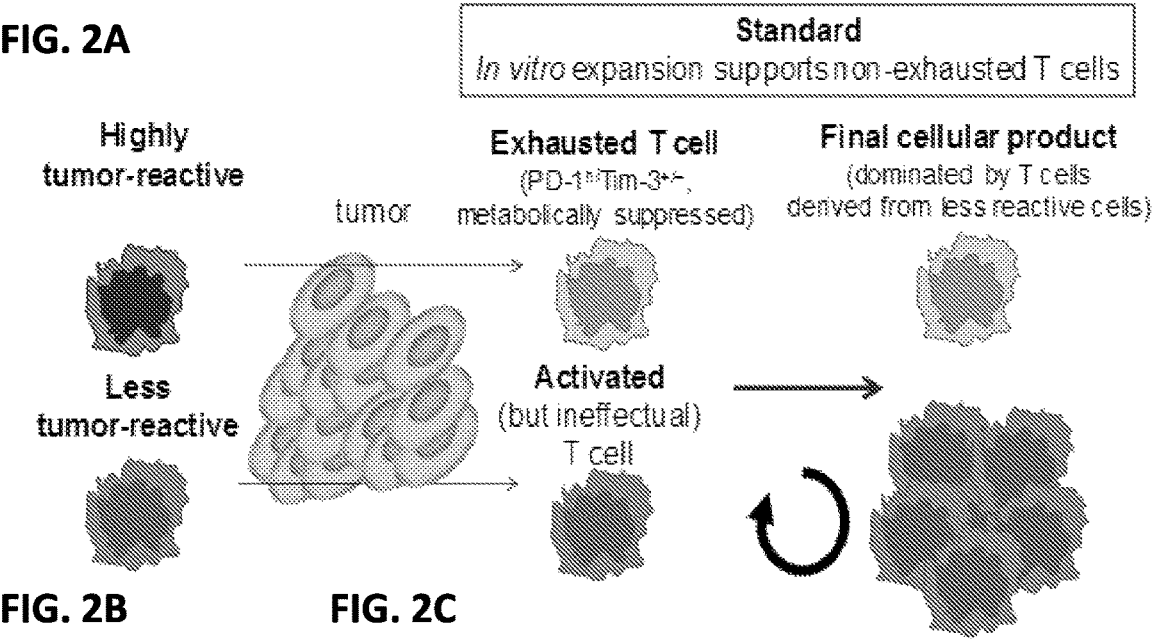
FIGS. 2A-2C. Schematic and rationale for metabolic support of exhausted T cell expansion. A, Phenotypically 'exhausted' T cells are derived from T cells that reacted heavily to tumor in the past, but due to their persistent metabolic deficiencies, are likely poorly represented in the final cellular product of direct ex vivo expansion. B, Metabolically insufficiency of exhausted T cells is stable in ex vivo culture. MitoTracker® FM fluorescent dye (mitochondrial mass) staining of T cells sorted directly ex vivo from LN or B16 TIL, then analyzed or activated for 5 d with anti-CD3, anti-CD28, and 10 U/mL IL-2. C, If mitochondrial biogenesis were to be stimulated using pharmacologic activation/stabilization of PGC1α, we would hypothesize that T cells that were previously 'exhausted' would be more proliferative, thus being more represented after long-term ex vivo culture.
Figure 2B:
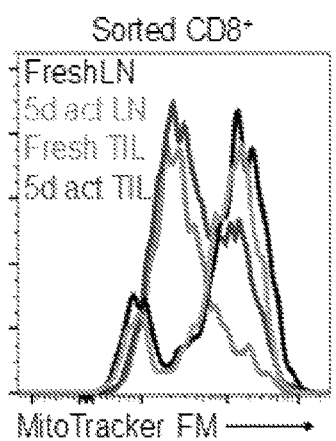

This disclosure provides methods for correcting the cellular defect in exhausted T cells to improve adoptive TIL therapy (for example in a subject with cancer). As T cell exhaustion is driven through chronic activation of the TCR, exhausted T cells can be used for expansion, as they have likely been heavily reactive to tumor antigens[14]. However, it is shown therein that the mitochondrial dysfunction found in exhausted T cells is a stable phenotype that persists even after culture outside of the tumor microenvironment (FIGS. 2A, 2B). Thus, due to their inherent metabolic dysfunction, during the rapid expansion protocols utilized to culture these T cells, they likely cannot proliferate effectively and may be eventually diluted out by their less exhausted counterparts (FIG. 2A). In other words, rapid expansion actually selects against the most desirable cells.

Figure 2C:
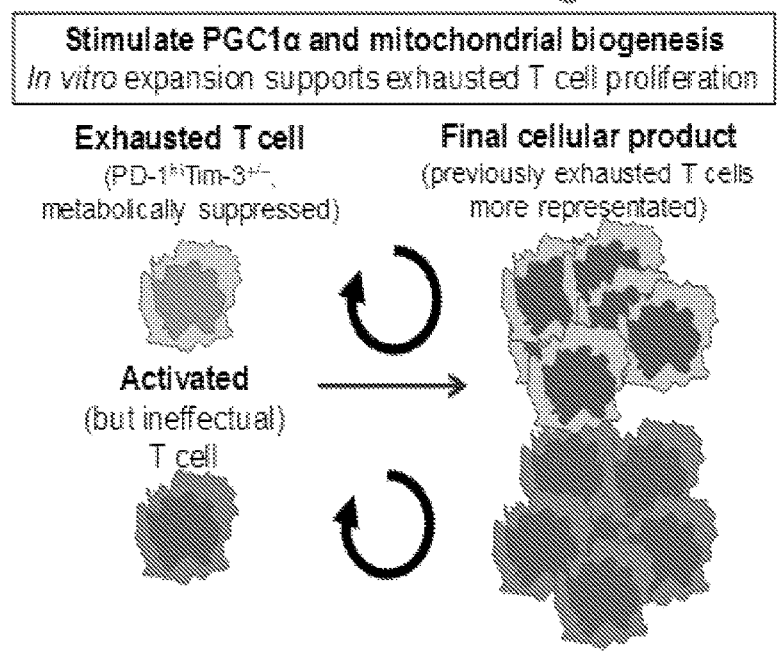

Based on these observations, this disclosure provides methods that utilize pharmacologic agents to stimulate the PGC1α axis in cells from TIL, a key node of metabolic dysregulation in intratumoral T cell exhaustion. By stimulating PGC1α in vivo, ex vivo, or both, mitochondrial biogenesis is enhanced in the tumor-infiltrating T cells that lack mitochondria, and this 'rejuvenation' will allow the exhausted T cells to more effectively proliferate and expand (FIG. 2C). The result is to 'level the playing field' in the in vitro expansion, such that the highly tumor reactive, previously exhausted T cells expand equally, leading to higher representation in the final cellular product. As only exhausted T cells harbor this metabolic defect, restoration of mitochondrial function can selectively boost the proliferation and function of exhausted T cells. This solves a problem that likely cannot be solved solely by optimization of cytokine levels and stimulation periods utilized during rapid expansion protocols.

Restoration of Exhausted TILs

Provided herein are methods for treating exhausted TILs, such as tumor infiltrating T-cells, thereby producing restored TILs, such as restored TIL T cells. In some examples, the TILs from the tumor that are to be treated include exhausted tumor infiltrating T-cells, such as those having sustained expression of PD-1, sustained expression of LAG-3, sustained expression of Tim-3, reduced mitochondrial mass, reduced expression of PGC1α, or combinations thereof.

The disclosed methods utilize effective amounts of one or more agents that increase peroxisome proliferator-activated receptor gamma coactivator 1-alpha (PGC1α) activity in the TILs. Such methods can include ex vivo steps, such as those that occur in culture, for example to treat (e.g., restore or recover) the exhausted TILs and expand the TILs. Such methods can include in vivo steps, such as those that occur in the body, for example to treat (e.g., restore or recover) the exhausted TILs and expand the TILs. Such methods can also include combinations of ex vivo and in vivo steps. Exemplary combinations of steps that can be used in the disclosed methods are shown in the Table below.

Exemplary Steps to Restore Exhausted T Cells

|  | Example 1 | Example 2 | Example 3 | Example 4 |
| --- | --- | --- | --- | --- |
| Administer PGC1α to a subject with a tumor | x | x |  | x |
| Harvest/isolate TILs from tumor | x | x | x |  |
| Expand TILs from tumor ex vivo in the presence of PGC1α | x |  | x |  |
| Expand TILs from tumor ex vivo without PGC1α |  | x |  |  |

Such ex vivo steps can include incubating TILs obtained from a tumor in the presence of one or more PGC1α agonists (such as at least 2, at least 3, at least 4, or at least 5 different agents, such as 1, 2, 3, 4, 5, 6, 7, 8, 9, or 10 agents) under conditions that allow for expansion of the TILs and restoration of the exhausted tumor-infiltrating T-cells. In some examples, ex vivo treatment can include incubating the TILs in a culture medium, such as serum-free media (e.g., AIM V® medium) or human AB serum. The method of ex vivo treatment can further include contacting the TILs from the tumor with a gamma-chain cytokine (such as interleukin 2 (IL-2) and/or IL-15), anti-CD3, anti-CD28, or combinations thereof. In some examples, the anti-CD3 and the anti-CD28 are present on a bead. The amount of anti-CD3, anti-CD28 and IL-2 can vary, such as from 3-10 µg/mL anti-CD3 (immobilized), 2-10 µg/mL anti-CD28, and 10 U/mL to 6000 U/mL IL-2. In some examples, additional agents are present in the ex vivo culture, such as gamma chain cytokines (as well as reagents provided in U.S. Pat. No. 5,126,132). In typical examples, the TILs are treated and expanded ex vivo at 37° C.

Such methods can include in vivo steps, such as those that occur in the body, for example to treat (e.g., restore) the exhausted TILs. Such in vivo steps can include administering an effective amount of one or more agents that increase PGC1α activity to a subject with the tumor. For example, the method can include administering an effective amount of one or more agents that increase PGC1α activity (such as pioglitazone, rosiglitazone, rivoglitazone, or troglitazone) to the subject with the tumor. In some examples, the subject is treated for a period of days or weeks (such as s at least 1 day, at least 2 days, at least 3 days, at least 4 days, at least 5 days, at least 6 days, at least 1 week, at least 2 weeks, at least 3 weeks, at least 4 weeks, or at least 6 weeks, such as 1 day, 2 days, 3 days, 4 days, 5 days, 6 days, 1 week, 2 weeks, 3 weeks, 4 weeks, 6 weeks, such as 2 to 7 days or 2 to 5 days). In some examples, such methods are followed by harvesting or obtaining TILs from the tumor. The resulting TILs from the tumor of the subject treated with the one or more agents that increase PGC1α activity can then be expanded ex vivo, for example presence of one or more PGC1α agonists (such as at least 2, at least 3, at least 4, or at least 5 different agents, such as 1, 2, 3, 4, 5, 6, 7, 8, 9, or 10 agents) under conditions that allow for expansion of the TILs and restoration of the exhausted tumor-infiltrating T-cells. In some examples, ex vivo treatment can include incubating the TILs in a culture medium, such as serum-free media (e.g., AIM V® medium) or human AB serum. The method of ex vivo treatment can further include contacting the TILs from the tumor with a gamma-chain cytokine (such as interleukin 2 (IL-2) and/or IL-15), anti-CD3, anti-CD28, or combinations thereof. In some examples, the anti-CD3 and the anti-CD28 are present on a bead. The amount of anti-CD3, anti-CD28 and IL-2 can vary, such as from 3-10 µg/mL anti-CD3 (immobilized), 2-10 µg/mL anti-CD28, and 10 U/mL to 6000 U/mL IL-2. In some examples, additional agents are present in the ex vivo culture, such as gamma chain cytokines (as well as reagents provided in U.S. Pat. No. 5,126,132). In typical examples, the TILs are treated and expanded ex vivo at 37° C. In some examples, the resulting TILs from the tumor of the subject treated with the one or more agents that increase PGC1α activity are then expanded ex vivo in the absence of the PGC1α agonist(s) (e.g., in the presence of IL2).

Restoration of exhausted tumor-infiltrating T-cells can include increasing PGC1α nucleic acid and/or protein expression, increasing PGC1α activity (e.g., as indicated by increasing mitochondrial activity [e.g., oxidative metabolism] and/or mitochondrial mass). In some examples, the TILs obtained from a tumor (for example from a subject who was or was not previously administered one or more PGC1α agonists) are incubated ex vivo (for example in the presence of one or more PGC1α agonists, though the one or more PGC1α agonists is not required (but can be included) if the subject was administered one or more PGC1α agonists prior to harvesting the TILs, for example within 1 to 7 days prior) to allow for sufficient expansion (e.g., reproduction of the TILs) as needed for transplantation, such as a period of days or weeks (such as at least 1 week, at least 2 weeks, at least 3 weeks, at least 4 weeks, or at least 6 weeks). In some examples, the TILs are allowed to expand until millions or billions of TILs are obtained, such as tens of billions TILs.

Thus, in some examples, the methods of restoring TILs, such as TIL T cells, increases PGC1α protein expression in the exhausted tumor-infiltrating T-cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%, for example as compared to an amount of PGC1α protein expression prior to treatment with the PGC1α agonist. In some examples, contacting the TILs ex vivo with the PGC1α agonist increases mitochondrial activity (e.g., oxidative metabolism) in the exhausted tumor-infiltrating T-cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%, for example as compared to an amount of PGC1α protein expression prior to treatment with the PGC1α agonist. In some examples, contacting the TILs ex vivo with the PGC1α agonist increases mitochondrial mass in the exhausted tumor-infiltrating T-cells by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%, for example as compared to an amount of PGC1α protein expression prior to treatment with the PGC1α agonist. In some examples, combinations of these effects are achieved.

In some examples, the method includes monitoring the expanding TILs, for example determining the number of cells, determining or measuring the mitochondrial activity (e.g., oxidative metabolism) of the TILs, determining or measuring the mitochondrial mass of the TILs, determining or measuring nucleic acid and/or protein expression of one or more of PGC1α, PD-1, LAG-3, and Tim-3 in the TILs, or combinations thereof.

In some examples, TILs from the tumor are isolated prior to expanding them ex vivo, for example by isolating $CD8^+$ T cells from the tumor (e.g., using flow cytometry). Thus, for example, the tumor can be minced or homogenized, and T cells separated from tumor cells. In some examples, a portion of the tumor from the subject is incubated with the PGC1α agonist(s) (and optional other agents such as IL-2, anti-CD3, and/or anti-CD28), under conditions that allow reproduction of the T cells (and rescue of the exhausted tumor infiltrating T-cells) in the tumor sample. Exemplary methods for isolating T cells from the tumor are provided in Rosenberg et al., *Clin. Cancer Res.* 17:4550-7, 2011 and Gros et al., *J. Clin. Invest.* 124:2246-59, 2014.

Methods of Using Restored and Expanded TILs

TILs treated and expanded using the disclosed methods can be used in cancer immunotherapy, for example to treat a tumor in vivo (for a general overview of such methods, see for example see Phan and Rosenberg, *Cancer Control* 20:289-97, 2013, herein incorporated by reference). For example, an effective amount of the expanded TILs (such as at least $5\times10^9$ TILs, at least $5\times10^{19}$, or at least $5\times10^{11}$ TILs) generated using the methods herein are administered to the subject, thereby treating a tumor (such as a primary tumor and/or a metastasis) in the subject. In some examples, such subjects are also administered an effective amount of IL-2 (such as 10,000 to 100,000 units/kg body weight) to the subject before, after, or both before and after, administering the expanded TILs. In some examples, such subjects are also administered an effective amount of one or more agents that increase PGC1α activity before, after, or both before and after, administering the expanded TILs. for example, subjects can be administered an effective amount of one or more agents that increase PGC1α activity for at least 1 week, at least 2 weeks, at least 4 weeks, at least 2 months, at least 3 months, at least 6 months, at least 9 months, at least 1 year, at least 2 years, or at least 5 years, after receiving the expanded TILs.

In some examples, the subject is administered an effective amount of nonmyeloablative chemotherapy or radiotherapy to deplete native lymphocytes prior to administering an effective amount of the expanded TILs. For example, the subject may receive an effective amount of nonmyeloablative chemotherapy, such as administration of one or more of cisplatin, fludarabine, idarubicin, melphalan, ara-C, 2-chlorodeoxyadenosine, antithymocyte globulin, and cyclophosphamide (such as 10 to 50 mg/kg body weight). In some examples, the subject receive an effective amount of solid tumor irradiation, thymic irradiation, or total body irradiation (e.g., 2 Gy), or combinations thereof. Other specific examples are provided in Phan and Rosenberg, *Cancer Control* 20:289-97, 2013.

In some examples, following administration of the TILs, the subject is administered one or more of an effective amount of tacrolimus, cyclosporine, and/or methotrexate.

Such methods can treat the tumor in the subject by reducing the volume or weight of the tumor, reducing the number of metastases, reducing the size or weight of a metastasis, or combinations thereof. In some examples a metastasis is cutaneous or subcutaneous. Thus, in some examples, administration of TILs expanded using the disclosed methods treats a tumor in a subject by reducing the size or volume of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of TILs or administration of TILs produced using a method that does not include culturing of the TILs in the presence of a PGC1α agonist. In some examples, administration of TILs expanded using the disclosed methods treats a tumor in a subject by reducing the weight of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of TILs or administration of TILs produced using a method that does not include culturing of the TILs in the presence of a PGC1α agonist. In some examples, administration of TILs expanded using the disclosed methods treats a tumor in a subject by reducing the size or volume of a metastasis by at least 10%, at least 20%, at least 30%, at least 40%, at least 50%, at least 60%, at least 70%, at least 75%, at least 80%, at least 90%, at least 95%, at least 98% or at least 99%, for example as compared to no administration of TILs or administration of TILs produced using a method that does not include culturing of the TILs in the presence of a PGC1α agonist. In some examples, administration of TILs expanded using the disclosed methods treats a tumor in a subject by reducing the number of metastases by at least 10%, at least 20%, at least 30%, at least 40%, at least 50%, at least 60%, at least 70%, at least 75%, at least 80%, at least 90%, at least 95%, at least 98% or at least 99%, for example as compared to no administration of TILs or administration of TILs produced using a method that does not include culturing of the TILs in the presence of a PGC1α agonist. In some examples, administration of TILs expanded using the disclosed methods treats a tumor in a subject by increasing the survival time of the subject with the tumor by at least 10%, at least 20%, at least 30%, at least 40%, at least 50%, at least 60%, at least 70%, at least 75%, at least 80%, at least 90%, at least 95%, at least 100%, at least 200%, at least 300%, at least 400%, or at least 500%, for example as compared to no administration of TILs or administration of TILs produced using a method that does not include culturing of the TILs in the presence of a PGC1α agonist. In some examples, administration of TILs expanded using the disclosed methods treats a tumor in a subject by increasing the survival time of the subject by at least 1 month, at least 3 months, at least 6 months, at least 9 months, at least 1 year, at least 2 years, at least 3 years, at least 4 years, or at least 5 years, for example as compared to no administration of TILs or administration of TILs produced using a method that does not include culturing of the TILs in the presence of a PGC1α agonist. In some examples, combinations of these effects are achieved.

Exemplary tumors that can be treated include, but are not limited to, colorectal cancer, melanoma, cervical cancer, lung cancer, ovarian cancer, bladder cancer, breast cancer, or head and neck cancer. Other exemplary cancers are provided herein.

In some examples the subject administered expanded and restored TILs was previously treated unsuccessfully with a chemotherapy, radiation therapy, biologic therapy, or combinations thereof (e.g., the tumor in the subject did not significantly decrease in size or even increased in size, and/or metastasized). In some examples the subject administered an effective amount of expanded and restored TILs has a tumor that was not responsive to a PD-1 antagonist or a PD-L1 antagonist (e.g., the tumor in the subject did not significantly decrease in size or even increased in size, and/or metastasized), such as an antibody that specifically binds PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C.

Compositions and Kits

Also provided are compositions and kits that can be used with the disclosed methods.

Provided are isolated TILs expanded using the disclosed methods. In some examples, such expanded TILs are restored tumor-infiltrating T-cells that were previously exhausted (e.g., have increased PGC1α protein expression relative to PGC1α protein expression of exhausted TILs). In some examples, the isolated TILs expanded using the disclosed methods are present in a pharmaceutically acceptable carrier. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, PA, 21" Edition (2005). For instance, fluid vehicles such as water, physiological saline, other balanced salt solutions, aqueous dextrose, glycerol or the like can be present. In addition to biologically-neutral carriers, pharmaceutical compositions that include isolated TILs expanded using the disclosed methods are present can contain minor amounts of non-toxic auxiliary substances, such as wetting or emulsifying agents, preservatives, pH buffering agents, or the like, for example sodium acetate or sorbitan monolaurate.

In some examples, the isolated TILs expanded using the disclosed methods are present in a growth media, such as such as serum-free media (e.g., AIM V® medium) or human AB serum. In some examples, the isolated TILs expanded using the disclosed methods are present in a preservative, such as DMSO. In some examples, the isolated TILs expanded using the disclosed methods are cryopreserved.

In some examples, the composition or kit includes one or more agents that increase PGC1α activity (such as 1, 2, 3, 4 or 5 different PGC1α agonists) and one or more of anti-CD3, anti-CD28, IL-2, and IL-15. In some examples the composition or kit includes one or more agents that increase PGC1α activity (such as those described herein), anti-CD3, anti-CD28, and IL-2. In some examples, in a kit, such reagents are present in a separate container. In one example, anti-CD3 and anti-CD28 are in the same container, and may be present on (e.g., attached to) a bead, for example.

In some examples the kit or composition includes media in which the TILs can be cultures or expanded ex vivo, such as AIM V® media.

In some examples the kit or composition includes an antimicrobial agent, such as tacrolimus, cyclosporine, and/or methotrexate.

PGC1α Agonists

Pharmacologic agents which can increase PGC1α activity include but are not limited to PPARγ agonists, AMPK agonists, sirtuin agonists, and combinations thereof.

In one example, the pharmacologic agent used to increase PGC1α activity in a tumor-infiltrating T cell (such as an exhausted T-cell) includes one or more PPARγ agonists. In some examples, a PPARγ agonist increases PGC1α activity in a TIL T-cell by at least 10%, at least 20%, at least 25%, at least 30%, at least 40%, at least 50%, at least 60%, at least 70%, at least 75%, at least 80%, at least 90%, at least 100%, at least 200%, at least 300%, at least 400%, or at least 500% (e.g., as compared to the absence of the PPARγ agonist). Examples of PPARγ agonists include, but are not limited to, a thiazolidinedione (TZD) (also known as glitazone), aleglitazar, farglitazar, muraglitazar, or tesaglitazar. TZDs contain a functional group in which thiazolidine serves as a dione. Examples of TZDs include, but are not limited to, pioglitazone, rosiglitazone, rivoglitazone, and troglitazone.

In one example, the pharmacologic agent used to increase PGC1α activity in a tumor-infiltrating T cell (such as an exhausted T-cell) includes one or more AMP-activated protein kinase (AMPK) activators or agonists. In some examples, an AMPK agonist increases PGC1α activity in a tumor-infiltrating T-cell by at least 10%, at least 20%, at least 25%, at least 30%, at least 40%, at least 50%, at least 60%, at least 70%, at least 75%, at least 80%, at least 90%, at least 100%, at least 200%, at least 300%, at least 400%, or at least 500% (e.g., as compared to the absence of the AMPK agonist). Examples of AMPK agonists include, but are not limited to, 5-aminoimidazole-4-carboxamide ribonucleotide (AICAR) and D942.

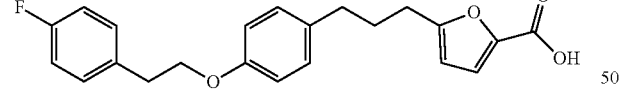

D942

In one example, the pharmacologic agent used to increase PGC1α activity in a tumor-infiltrating T cell (such as an exhausted T-cell) includes one or more Sirtuin-activating compounds (STAC). STACs are chemical compounds having an effect on sirtuins (such as sirtuin 1), a group of enzymes that use NAD+ to remove acetyl groups from proteins. In some examples, an STAC increases PGC1α activity in a tumor-infiltrating T-cell by at least 10%, at least 20%, at least 25%, at least 30%, at least 40%, at least 50%, at least 60%, at least 70%, at least 75%, at least 80%, at least 90%, at least 100%, at least 200%, at least 300%, at least 400%, or at least 500% (e.g., as compared to the absence of the AMPK agonist). Examples of STACs include, but are not limited to, SRT1720, SRT2104 (GSK2245840), SRT2183, SRT1460, and resveratrol.

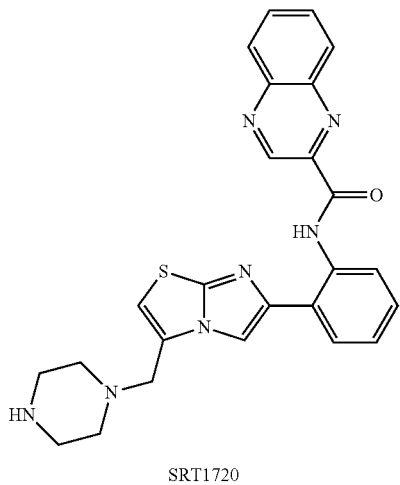

SRT1720

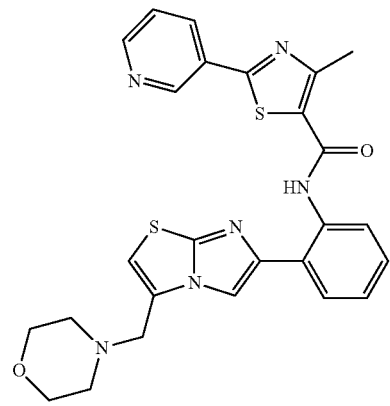

SRT2104 (GSK2245840)

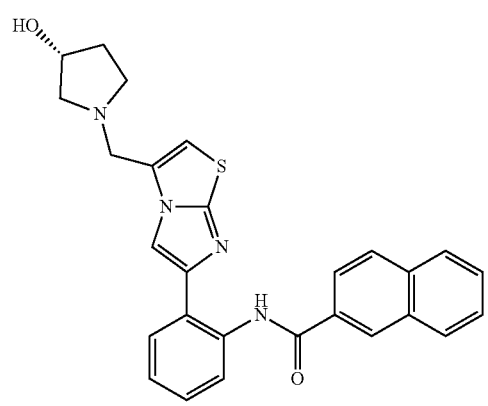

SRT2183

-continued

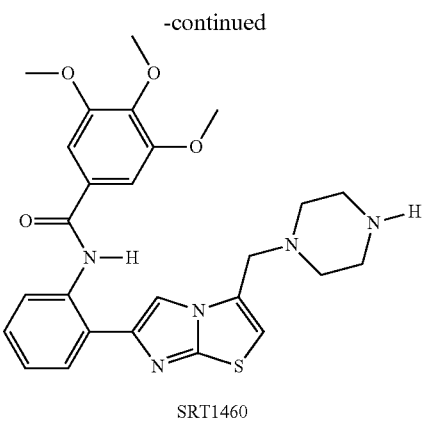

SRT1460

In some examples, the pharmacologic agent used to increase PGC1α activity (e.g., PPARγ agonist, AMPK agonist, sirtuin agonist, or combinations thereof) is used at a dose of at least 0.01 µM, at least 0.1 µM, at least 1 µM, at least 10 µM, at least 20 µM, at least 50 µM, or at least 10 µM, such as 0.1 to 20 µM, 1 to 20 µM, 5 to 10 µM, or 1 to 5 µM. In some examples, the pharmacologic agent(s) used to increase PGC1α activity is incubated with the TILs for a short-term (e.g., 5-7 days, such as 5, 6, or 7 days) or long-term (e.g., 14-21 days, such as 14, 15, 16, 17, 18, 19, 20, or 21 days).

In some examples, the pharmacologic agent used to increase PGC1α activity is pioglitazone (e.g., in vivo at a dose of 15 mg to 45 mg orally, such as 15 mg, 30 mg, or 45 mg once daily, or 10 µM to 100 µM ex vivo, such as 10 µM, 50 µM or 100 µM). In some examples, the pharmacologic agent used to increase PGC1α activity is rosiglitazone (e.g., in vivo at a dose of 2 mg to 8 mg orally, such as 2 mg, 4 mg, or 8 mg once daily, or 50 µM to 500 µM ex vivo, such as 50 µM, 100 µM or 200 µM). In some examples, the pharmacologic agent used to increase PGC1α activity is rivoglitazone (e.g., in vivo at a dose of 0.5 mg to 2 mg orally, such as 0.5 mg, 1 mg, 1.5 mg, or 2 mg once daily, or 50 µM to 500 µM ex vivo, such as 50 µM, 100 µM or 200 µM). In some examples, the pharmacologic agent used to increase PGC1α activity is troglitazone (e.g., in vivo at a dose of 200 mg to 600 mg orally, such as 200 mg, 300 mg, 400 mg, or 600 mg once daily, or 50 µM to 500 µM ex vivo, such as 50 µM, 100 µM or 200 µM). In some examples, the pharmacologic agent used to increase PGC1α activity is aleglitazar (e.g., in vivo at a dose of 10 µg to 100 µg orally, such as 10 µg, 20 µg, 50 µg, or 100 µg once daily, or 10 to 100 µM ex vivo, such as 10 µM, 50 µM or 100 µM). In some examples, the pharmacologic agent used to increase PGC1α activity is farglitazar (e.g., in vivo at a dose of 0.5 mg to 2 mg orally, such as 0.5 mg, 1 mg, 1.5 mg, or 2 mg once daily, or 5 µM to 100 µM ex vivo, such as 5 µM, 10 µM, 50 µM or 100 µM). In some examples, the pharmacologic agent used to increase PGC1α activity is muraglitazar (e.g., in vivo at a dose of 0.4 mg/kg to 300 mg/kg orally, such as 0.4 mg/kg, 1 mg/kg, 2 mg/kg, or 4 mg/kg once daily or 5 µM to 100 µM ex vivo, such as 5 µM, 10 µM, 50 µM or 100 µM). In some examples, the pharmacologic agent used to increase PGC1α activity is tesaglitazar (e.g., in vivo at a dose of 0.1 mg to 3 mg orally, such as 0.1 mg, 0.5 mg, 1 mg, 2 mg, or 3 mg once daily, or 5 µM to 100 µM ex vivo, such as 5 µM, 10 µM, 50 µM or 100 µM). In some examples, the pharmacologic agent used to increase PGC1α activity is AICAR (e.g., in vivo at a dose of 10 mg/kg to 500 mg/kg i.v., such as 10 mg/kg, 20 mg/kg, 50 mg/kg, 50 mg/kg, 250 mg/kg, or 500 mg/kg once daily or 5 µM to 100 µM ex vivo, such as 5 µM to 50 µM, 5 µM, 10 µM, 50 µM or 100 µM). In some examples, the pharmacologic agent used to increase PGC1α activity is resveratrol (e.g., in vivo at a dose of 20 mg to 200 mg orally, such as 20 mg, 50 mg, 100 mg, or 200 mg once daily or 5 µM to 100 µM ex vivo, such as 5 µM, 10 µM, 50 µM or 100 µM).

Example 1

Comparison of Proliferative Capacities of 'Exhausted' Subsets of TILs

Utilizing T cells sorted from murine tumors, it can be demonstrated that exhausted T cells, identified by either co-inhibitory molecule expression or low mitochondrial mass, are outproliferated by their less exhausted (but also less tumor reactive) brethren.

Preliminary data indicate that T cells that infiltrate human and murine tumors display a phenotype of metabolic insufficiency, most prominently characterized by a crippling loss of mitochondrial function and mass (FIGS. 1A, B). This correlates with upregulation of coinhibitory molecule markers of T cell exhaustion, leading to in an inability to maintain ATP reserves (FIGS. 1C, D). This loss of mitochondrial mass underlies the dysfunctional phenotype of exhausted T cells in cancer. High numbers of exhausted T cells can be isolated from tumors, such as the B16 tumor model. B16 is both highly aggressive and insensitive to many immunotherapies.

Figure 3:
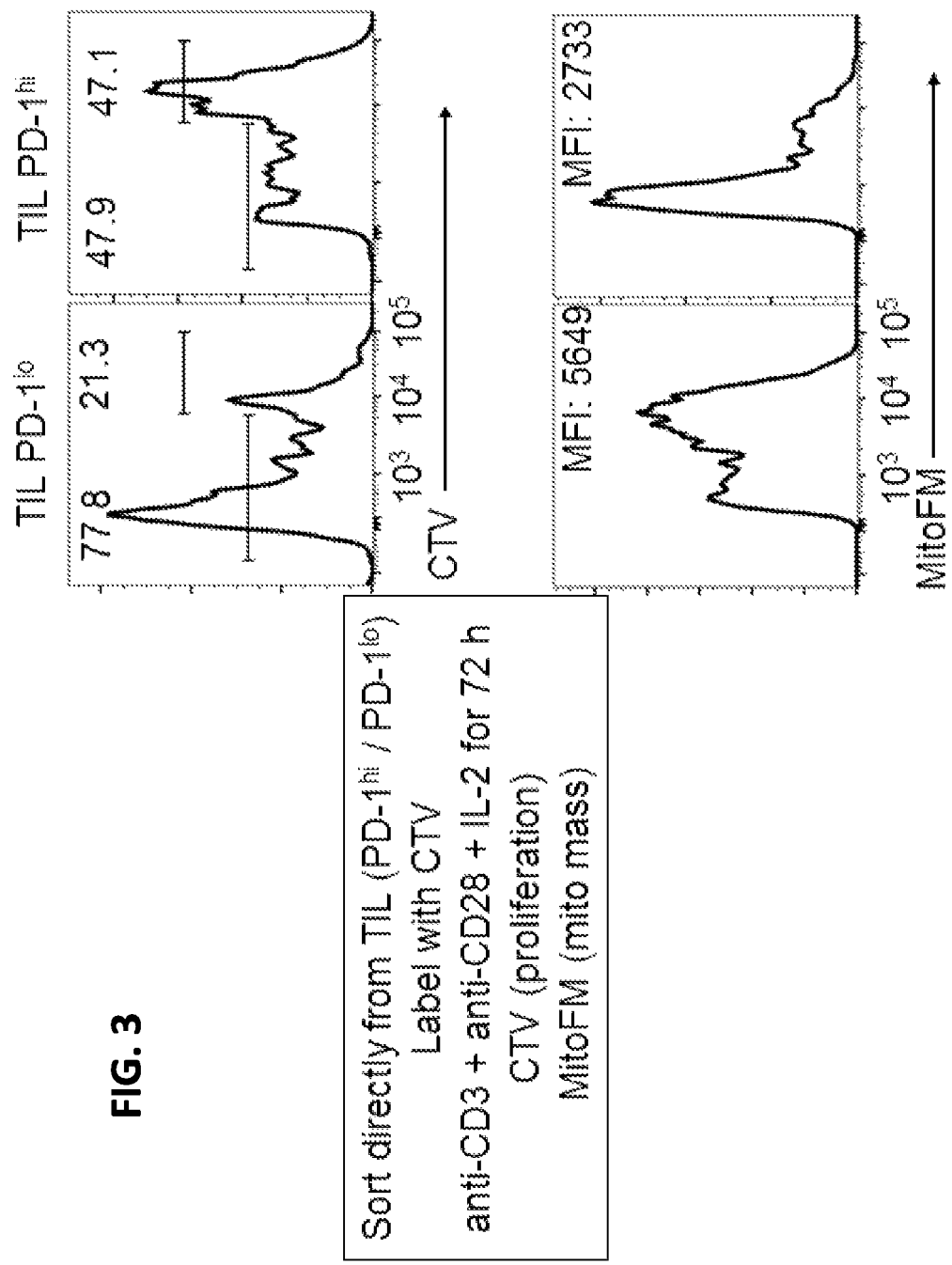
FIG. 3. PD-1$^{hi}$ cells remain mitochondrially deficient and fail to proliferate ex vivo. PD-1$^{lo}$ and PD-1$^{hi}$ cells were sorted from B16 melanomas, labeled with CellTrace® Violet dye, and stimulated with anti-CD3/anti-CD28/IL-2 for 72 h. Proliferation measured by CTV dilution and mito mass by Mito Tracker® FM fluorescent dye staining.

To confirm that exhausted T cells remain mitochondrially deficient in ex vivo culture, and that this negatively affects their proliferative/expansion capacity, the following methods can be used. C57/BL6 mice will be injected intradermally with B16 melanoma cells. After 12-14 d, tumors and lymph nodes will be harvested, and CD8$^+$ T cells will be sorted based on mitochondrial mass based on the expression of PD-1 and Tim-3. In some experiments, the T cells will be alternatively sorted based on their mitochondrial mass using MitoTracker® FM fluorescent dye staining. Cells will then be washed and labeled with CellTrace® Violet dye, and restimulated polyclonally with anti-CD3, anti-CD28, and IL-2. After 3 or 5 days, survival, proliferation, and metabolic capacity will be analyzed by flow cytometry and metabolic flux analysis, and the expansion potential of the cells will be calculated. It has been observed that PD-1$^{hi}$ T cells display a fundamental defect in mitochondrial mass that persists in ex vivo culture, and that this negatively impacts the ability of these cells to expand, especially compared to their PD-1$^{lo}$ counterparts (FIG. 3).

To demonstrate that exhausted T cells, despite having higher tumor reactivity, will not proliferate ex vivo due to fundamental metabolic defects and thus be unrepresented after multiple rounds of proliferation in culture, the following methods can be used. Congenically mismatched T cells will be used in a competitive setting. B16 melanoma cells will be implanted into either wild-type C57/BL6 mice (whose T cells express Thy1.2) or into B6.PL mice (congenic C57/BL6 whose T cells express Thy1.1). After tumors have progressed for 12-14 days, T cells will be isolated from the tumor or lymph node and sorted as described above. Cells expressing high or low levels of co-inhibitory molecules will then be mixed in a congenically mismatched fashion at a 1:1 ratio (PD$^{int}$Tim-3$^-$ from Thy1.1 mice and PD-1$^{hi}$Tim-3$^+$ from Thy1.2 mice and vice-versa). Then, the T cells will be stimulated polyclonally and cultured for several days in vitro using standard techniques.

Throughout T cell expansion culture, the relative proportion of Thy1.1+ to Thy1.2+ will be monitored by flow cytometry. It can be observed whether if, in a competitive stetting, the 'exhausted' T cells that previously reacted potently to tumors in vivo will be diluted out by less reactive cells during rapid expansion.

It is hypothesized that PD-1$^{hi}$Tim-3+ cells as well as T cells that have low mitochondrial mass will fail to proliferate in vitro as well as their non-exhausted counterparts. This will result in a final cellular product that will be heavily dominated by T cells derived from the 'non-exhausted' progenitors.

Example 2

Pharmacologic Strategies to 'Rejuvenate' Mitochondrial Function During Ex Vivo Expansion The mitochondrial biogenesis protein PGC1α was identified as a key node of dysregulation in exhausted T cells. Thus, this example describes methods that use pharmacologic agents that promote PGC1α activity, stability, or localization to reprogram T cell metabolism during in vitro expansion from tumors, and examine these rejuvenated cells functionally in vitro and in vivo.

The mitochondrial dysfunction observed in tumor-infiltrating T cells is caused in part by a failure to maintain mitochondrial biogenesis during chronic activation. This mitochondrial biogenesis machinery is characterized prominently by the transcriptional co-activator PPAR-gamma-coactivator 1 alpha (PGC1α)[12, 13], which is dramatically reduced in tumor-infiltrating T cells (FIG. 1E). Furthermore, loss of mitochondrial mass, especially in T cells expressing multiple co-inhibitory checkpoints, is a stable phenotype that is not simply rescued by culture outside of the tumor microenvironment (FIGS. 2A-2C). Thus, pharmacologically reactivating this mitochondrial biogenesis machinery can provide additional mitochondrial function to support the ex vivo expansion of exhausted T cells.

PGC1α is dynamically regulated at several levels, including its transcriptional expression levels, activity, and localization[12]. Pharmacologic agents which can amplify PGC1α activity by these mechanisms can be utilized: PPAR gamma agonists (e.g., rosiglitazone), AMPK activators (e.g., 5-aminoimidazole-4-carboxamide ribonucleotide or AICAR), and sirtuin activators (such as a sirtuin 1 activator) (e.g., resveratrol, SRT1720, and SRT2104).[16] Rosiglitazone is a PPAR gamma agonist which can promote mitochondrial biogenesis potentially through upregulating PGC1α expression[17, 18]. AICAR is an activator of AMPK, which phosphorylates PGC1α and promotes its activity, thus serving to activate pre-existing PGC1α.[16] Sirtuins (especially SIRT1) are deacetylases which promote PGC1α recruitment to target genes and transcriptional activity. Resveratrol, SRT1720, and SRT2104 are used, as they have been shown to activate SIRT1 and promote PGC1α activity and consequent mitochondrial biogenesis in a variety of cell types.[16]

Figures 4A, 4B:
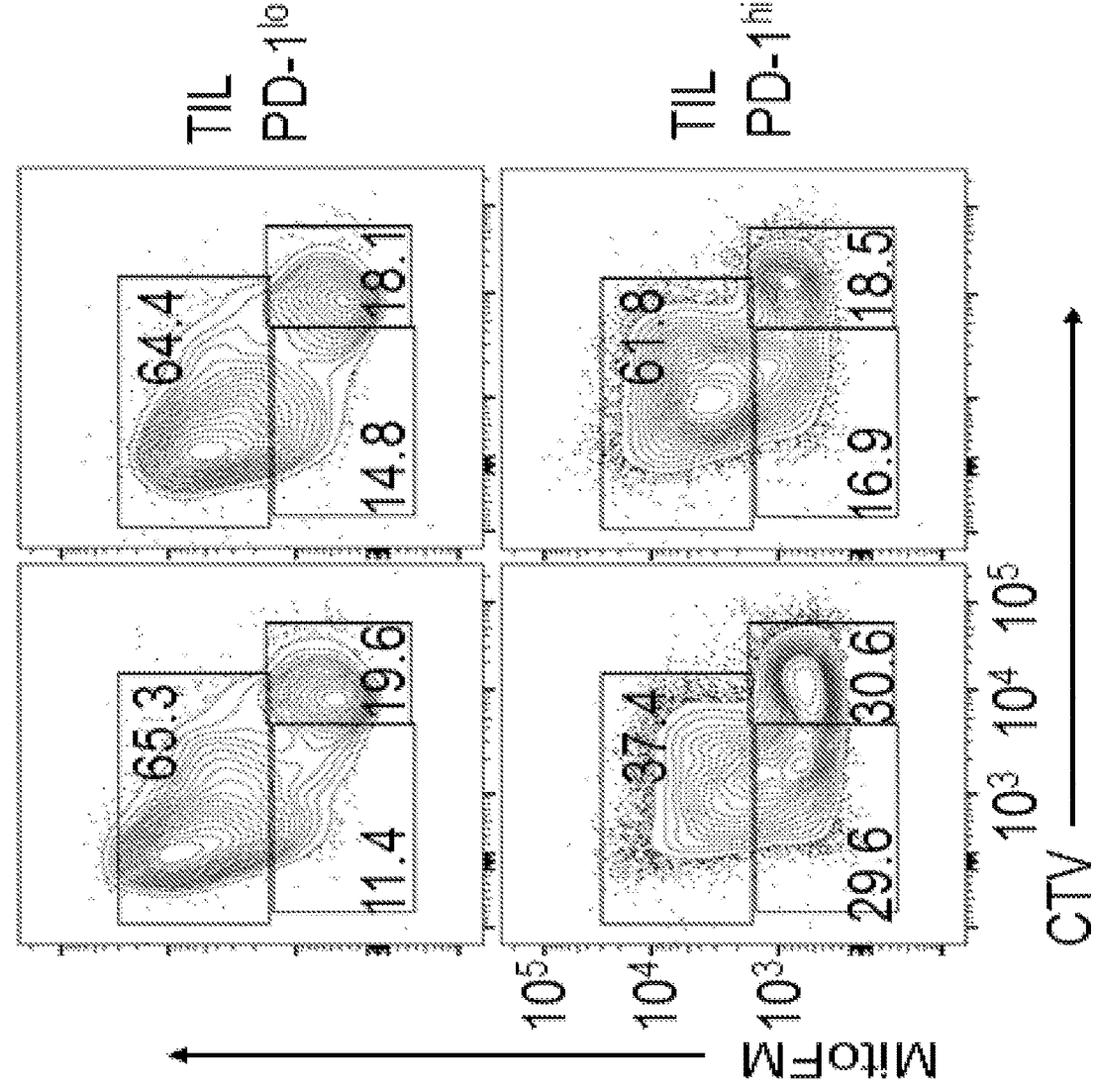
FIGS. 4A-4B. Rosiglitazone can rescue mitochondrial mass and proliferation. A, Flow cytogram of proliferation and mitochondrial mass of TIL cultures. T cells were sorted as in FIG. 3, but some were stimulated in the presence of 5 μM rosiglitazone. B, Live cell expansion (absolute numbers of $CD8^+$ T cells) cultured as in A.

The short-term effects of rosiglitazone, AICAR, and sirtuin activators on the metabolic and functional activity of ex vivo cultured tumor-infiltrating T cells can be examined as follows. To determine whether these pharmacologic activators can rejuvenate exhausted T cells, the sorting and culture strategies from Example 1 can be utilized. Specifically, PD-1−, PD1$^{hi}$, and PD-1$^{hi}$Tim-3+ T cells from B16 melanoma tumors will be labeled and stimulated polyclonally in vitro. However, in some cultures, media will be supplemented with rosiglitazone, AICAR, or sirtuin activators. After 72 h, proliferation (dye dilution), PGC1α expression (intracellular staining) and mitochondrial mass (MitoTracker® FM fluorescent dye staining) will be analyzed by flow cytometry, as well as metabolic flux analysis using Seahorse® technology. It has been observed has a dramatic effects on mitochondrial mass, and stimulates PD-1$^{hi}$ T cells to proliferate more effectively in vitro (FIGS. 4A, B).

The long-term effects of rosiglitazone, AICAR, and sirtuin activators on ex vivo cultured tumor-infiltrating T cells can be examined as follows. The congenic strategy described above is used to determine if long-term culture results in a higher representation of T cells that were 'previously exhausted.' Exhausted (PD-1$^{hi}$Tim-3+) T cells and tumor-infiltrating PD-1− T cells from congenically mismatched mice will be cocultured in the presence of optimized doses of our test agents. The culture will then be monitored for the relative abundance of the T cell populations; the final culture (10-14 days) will be assayed functionally for cytokine production (flow cytometry and ELISA). This will demonstrate that long-term, metabolic rejuvenation promotes the increased representation and function of 'previously exhausted' T cells.

The antitumor activity of 'rejuvenated' T cells can be examined using a model of TIL therapy in vivo. Total CD8+ TIL are isolated from d14 B16-bearing B6.PL (Thy1.1), and expanded in vitro using standard protocols or modified with the pharmacologic strategies developed earlier. After 7-14 days of in vitro expansion, w these T cells are adoptively transferred into new C57/BL6 mice bearing palpable B16 melanoma and monitor tumor growth and survival. In some experiments, a cohort of mice will be sacrificed early to interrogate the number and phenotype of the adoptively transferred mice based on Thy1.1 expression.

Once the T cells become metabolically sufficient, continued stimulation through the PGC1α axis might be unnecessary. If this is the case, kinetic analysis using the methods describe above can be used to determine when the drugs can be removed during the expansion procedure, thereby ameliorating any long-term toxicities these agents might show.

Example 3

Metabolic Rejuvenation of Human Tumor-Infiltrating T Cells

This example describes methods that can be used to treat human tumor-infiltrating T cells from head-and-neck cancer patients with one or more agents that promote mitochondrial biogenesis, assaying the resulting metabolic and proliferative capacities of the treated TILs as well as their effector function in vitro.

Human tumor-infiltrating T cells from head and neck cancer patient samples succumb to mitochondrial depletion and metabolic insufficiency (FIGS. 5A-5B). Because HNSCC shows mitochondrial suppression and high yields of T cells can be obtained from these samples, the in vitro culture methods described in Example 2 can be used for human T cell expansion and proliferation.

T cells are isolated from HNSCC samples using techniques adopted from Srivastava et al., *Cancer Immunol. Res* 3:936-45, 2015). Isolated T cells with then undergo flow cytometric purification based on PD-1 and Tim-3 expression and labeled with proliferation dyes. T cells will then be expanded using anti-CD3/CD28 coated beads and IL-2 in the presence or absence of metabolic agents (e.g., those in Example 2). After 3 and 5 days, T cell cultures will be sampled for flow cytometric analysis of proliferation by dye dilution, inhibitory molecule expression, and mitochondrial mass. If cellular yields allow, these cells will also be subjected to Seahorse® extracellular flux analysis to identify if metabolic pathways have been re-invigorated.

To ascertain whether rejuvenation promotes increased effector functions of T cells, cytokine production and cytotoxicity of tumor-infiltrating T cells will be tested. Human TIL will be expanded as described above. After expansion, T cells will be restimulated to examine cytokine production by flow cytometry and ELISA. In addition, T cells will be co-incubated with labeled target tumor cells, to determine whether they have increased cytolytic capacity.

Example 4

Restoration of Exhausted TIL T Cells Using Rosiglitazone (RSG)

This example describes methods used to enhance expansion of tumor infiltrating T cells using in vivo administration of rosiglitazone (RSG) prior to expansion ex vivo.

As shown in FIG. 6A, wild-type mice were injected with 125,000 B16 melanoma cells. Ten to twelve days later, mice were injected i.p. with PBS or RSG (100 ug/kg) for three consecutive days. TIL and lymph nodes (LN) were harvested from the treated mice, and expanded ex vivo for up to 14 days in the presence of IL2.

As shown in FIG. 6B, the tumor infiltrating T cells from mice administered RSG expanded more in culture than those from mice administered PBS. In addition, the tumor infiltrating T cells from mice administered RSG expand in culture to almost normal levels observed with T cells obtained from the lymph nodes (LN) (these are from mice treated with PBS only). Thus, the in vivo administration of RSG to treats the defect in the tumor infiltrating T cells, that is, revives exhausted TIL T cells. Treating mice with PGC1a antagonist rosiglitazone makes tumor infiltrating T cells expand more when they are activated and cultured in vitro for 14 days.

Example 5

Treatment of Tumors Using Rosiglitazone (RSG) Restored TIL T Cells

This example describes methods used to treat tumors in vivo by administration of rosiglitazone (RSG) followed by adoptive tumor T cell transfer.

Melanoma-specific T cells (p-mel1) were obtained from tumor-bearing mice, and expanded ex vivo for 10-14 days in the presence (RSG T cells) or absence (Veh T cell therapy) of 100 μM RSG. The expanded TIL T cells (1-3×10$^6$) were injected into mice bearing melanoma tumors, and tumors measured every 2 days. Some mice continued to receive RSG following the adoptive T cell transfer (RSG in vivo), while others did not (RST T cell therapy).

As shown in FIG. 7, untreated mice (no treatment) had tumors that were larger than any of the mice receiving the TIL T cell transfer. This rate decreased in mice that received TIL T cells not cultured with RSG (Veh T cell therapy), but a more significant decrease was achieved with TIL T cells that were cultured in the presence of RSG (RSG T cell therapy). Furthermore, the combination of TIL T cells expanded ex vivo in the presence of RSG, and subsequent in vivo administration of RSG, further increases the effectiveness of the TIL T cell transfer. In fact, some mice who received TIL T cells expanded in the presence of RSG and were administered RSG after the transfer ("RSG T Cells+ RSG in vivo") were cured of their tumors.

REFERENCES

1. Jiang et al. T-cell exhaustion in the tumor microenvironment. *Cell death & disease* 2015, 6: e1792.
2. Justus et al. Molecular Connections between Cancer Cell Metabolism and the Tumor Microenvironment. *International journal of molecular sciences* 2015, 16(5): 11055-11086.
3. Siska P J, Rathmell J C. T cell metabolic fitness in antitumor immunity. *Trends in immunology* 2015, 36(4): 257-264.
4. Xing et al. Metabolic reprogramming of the tumour microenvironment. *The FEBS journal* 2015, 282(20): 3892-3898.
5. Gajewski et al. Cancer immunotherapy strategies based on overcoming barriers within the tumor microenvironment. *Current opinion in immunology* 2013, 25(2): 268-276.
6. Hinrichs C S, Rosenberg S A. Exploiting the curative potential of adoptive T-cell therapy for cancer. *Immunological reviews* 2014, 257(1): 56-71.
7. Topalian et al., Immune Checkpoint Blockade: A Common Denominator Approach to Cancer Therapy. *Cancer Cell* 2015, 27(4): 450-461.
8. Harris D T, Kranz D M. Adoptive T Cell Therapies: A Comparison of T Cell Receptors and Chimeric Antigen Receptors. *Trends in pharmacological sciences* 2015.
9. Beavis et al. Reprogramming the tumor microenvironment to enhance adoptive cellular therapy. *Seminars in immunology* 2015.
10. Wherry E J, Kurachi M. Molecular and cellular insights into T cell exhaustion. *Nature reviews Immunology* 2015, 15(8): 486-499.
11. Delgoffe G M, Powell J D. Feeding an army: The metabolism of T cells in activation, anergy, and exhaustion. *Molecular immunology* 2015, 68 (2 Pt C): 492-496.
12. Finck B N, Kelly D P. PGC-1 coactivators: inducible regulators of energy metabolism in health and disease. *Journal of Clinical Investigation* 2006, 116(3): 615-622.
13. Spiegelman B M. Transcriptional control of energy homeostasis through the PGC1 coactivators. *Novartis Foundation symposium* 2007, 286: 3-6; discusssion 6-12, 162-163, 196-203.
14. Gros et al. PD-1 identifies the patient-specific CD8(+) tumor-reactive repertoire infiltrating human tumors. *The Journal of clinical investigation* 2014, 124(5): 2246-2259.
15. Delgoffe et al. Stability and function of regulatory T cells is maintained by a neuropilin-1-semaphorin-4a axis. *Nature* 2013, 501(7466): 252-256.
16. Komen J C, Thorburn D R. Turn up the power—pharmacological activation of mitochondrial biogenesis in mouse models. *Br. journal of pharmacology* 2014, 171(8): 1818-1836.
17. Rong et al. Rosiglitazone Induces Mitochondrial Biogenesis in Differentiated Murine 3T3-L1 and C3H/10T1/2 Adipocytes. *PPAR Research* 2011, 2011: 11.
18. Rong, et al. Adipose mitochondrial biogenesis is suppressed in db/db and high-fat diet-fed mice and improved by rosiglitazone. *Diabetes* 2007, 56(7): 1751-1760.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. I therefore claim as my invention all that comes within the scope and spirit of these claims.

The invention claimed is:

1. A method of expanding isolated exhausted tumor infiltrating lymphocytes (TILs) from a human or mouse subject, comprising: obtaining the exhausted TILs from a melanoma or head and neck cancer tumor of the human or mouse subject, wherein the exhausted TILs are $CD8^+ PD-1^{hi} Tim-3^+$ TILs; culturing the exhausted TILs ex vivo in the presence of rosiglitazone, interleukin 2 (IL-2), activating anti-human or mouse CD3 antibody, respectively, and activating anti-human or mouse CD28 antibody, respectively, thereby producing expanded TILs.

2. The method of claim 1, wherein the subject is a human.

3. The method of claim 1, wherein the tumor is a head and neck cancer.

4. The method of claim 1, wherein the tumor is a melanoma.

* * * * *